(12) United States Patent
Vocadlo et al.

(10) Patent No.: US 9,079,868 B2
(45) Date of Patent: Jul. 14, 2015

(54) SELECTIVE GLYCOSIDASE INHIBITORS AND USES THEREOF

(75) Inventors: David Jaro Vocadlo, Burnaby (CA); Ernest John McEachern, Burnaby (CA)

(73) Assignee: Simon Fraser University, Burnaby, BC (CA)

( * ) Notice: Subject to any disclaimer, the term of this patent is extended or adjusted under 35 U.S.C. 154(b) by 1106 days.

(21) Appl. No.: 13/057,065

(22) PCT Filed: Jul. 31, 2009

(86) PCT No.: PCT/CA2009/001088
§ 371 (c)(1),
(2), (4) Date: Jun. 10, 2011

(87) PCT Pub. No.: WO2010/012107
PCT Pub. Date: Feb. 4, 2010

(65) Prior Publication Data
US 2011/0237631 A1  Sep. 29, 2011

Related U.S. Application Data

(60) Provisional application No. 61/085,538, filed on Aug. 1, 2008.

(51) Int. Cl.
| | | |
|---|---|---|
| C07D 277/60 | (2006.01) | |
| C07D 263/52 | (2006.01) | |
| A61K 31/428 | (2006.01) | |
| A61K 31/423 | (2006.01) | |

(52) U.S. Cl.
CPC ............ *C07D 263/52* (2013.01); *A61K 31/423* (2013.01); *A61K 31/428* (2013.01); *C07D 277/60* (2013.01)

(58) Field of Classification Search
CPC .. C07D 277/60; C07D 263/52; A61K 31/428; A61K 31/423
See application file for complete search history.

(56) References Cited

U.S. PATENT DOCUMENTS

| | | |
|---|---|---|
| 8,334,310 B2 | 12/2012 | Vocadlo et al. |
| 8,541,441 B2 | 9/2013 | Vocadlo et al. |
| 2008/0287375 A1 | 11/2008 | Vocadlo et al. |
| 2011/0059668 A1 | 3/2011 | Bieser et al. |
| 2011/0301217 A1 | 12/2011 | Vocadlo et al. |
| 2012/0316207 A1 | 12/2012 | Vocadlo et al. |
| 2013/0131044 A1 | 5/2013 | Li et al. |
| 2014/0005191 A1 | 1/2014 | Coburn et al. |
| 2014/0018309 A1 | 1/2014 | Kaul et al. |
| 2014/0051719 A1 | 2/2014 | Vocadlo et al. |
| 2014/0088028 A1 | 3/2014 | Kaul et al. |
| 2014/0107044 A1 | 4/2014 | Mceachern et al. |

FOREIGN PATENT DOCUMENTS

| | | |
|---|---|---|
| JP | 11349541 A | 12/1999 |
| WO | 03/009808 A2 | 2/2003 |
| WO | 2012/064680 | 5/2012 |
| WO | 2013/000084 | 1/2013 |
| WO | 2013/000085 | 1/2013 |
| WO | 2013/000086 | 1/2013 |
| WO | 2013/025452 | 2/2013 |
| WO | 2013/169576 | 11/2013 |
| WO | 2014/032184 | 3/2014 |
| WO | 2014/032185 | 3/2014 |
| WO | 2014/032187 | 3/2014 |
| WO | 2014/032188 | 3/2014 |
| WO | 2014/067003 | 3/2014 |
| WO | 2014/105662 | 7/2014 |

OTHER PUBLICATIONS

Registry entry for CAS Registry for 103766-13-8, which entered STN on Aug. 18, 1986.*
Simpkins et al. J. Chem. Soc. Perkin Trans. 1: Organic and Bio-Organic Chemistry, 1992, 19, 2471-2477.*
Blattner et al. J. Chem. Soc. Perkin Trans. 1: Organic and Bio-Organic Chemistry, 1994, 23, 3411-3421.*
Griffith et al. J. Am. Chem. Soc. 1991, 113, 5863-5864.*
Arias, E.B., et al., Prolonged incubation in PUGNAc results in increased protein O-Linked glycosylation and insulin resistance in rat skeletal muscle. Diabetes 2004;53(4):921-930.
Bennett, R.A. and Pegg, A.E., Alkylation of DNA in rat tissues following administration of streptozotocin. Cancer Res 1981;41(7):2786-2790.
Bertram, L., et al., Evidence for genetic linkage of Alzheimer's disease to chromosome 10q. Science 2000;290 (5500):2302-2303.
Blattner, R., et al., Syntheses of the fungicide and insecticide allosamidin and a structural isomer. J Chem Soc Perkin Trans 1 1994;23:3411-3421.
Bounelis, P., et al., Glucosamine Provides Protection From Ischemia/Reperfusion Injury and Calcium Overload in Isolated Hearts and Leads to an Increase in O-Linked Glycosylation: 170. Shock 2004;21 170 Suppl 2:58.

(Continued)

*Primary Examiner* — Matthew Coughlin
(74) *Attorney, Agent, or Firm* — Greenberg Traurig, LLP; Chinh H. Pham; Fang Xie

(57) ABSTRACT

The invention provides compounds of Formula (I) for selectively inhibiting glycosidases, prodrugs of the compounds, and pharmaceutical compositions including the compounds or prodrugs of the compounds. The invention also provides methods of treating diseases and disorders related to deficiency or overexpression of O-GlcNAcase, accumulation or deficiency of O-GlcN Ac.

(I)

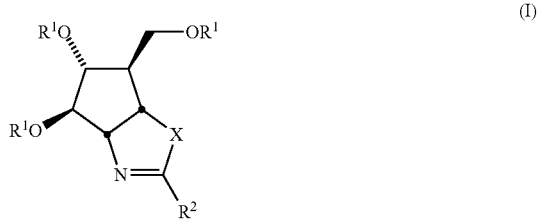

4 Claims, No Drawings

(56) References Cited

OTHER PUBLICATIONS

Braidman, I., et al., Separation and properties of human brain hexosaminidase C. Biochem J 1974;143(2):295-301.

Brickley, K., et al., GRIF-1 and OIP106, members of a novel gene family of coiled-coil domain proteins: association in vivo and in vitro with kinesin. J Biol Chem 2005;280(15):14723-14732.

Burkart, V., et al., Mice lacking the poly(ADP-ribose) polymerase gene are resistant to pancreatic beta-cell destruction and diabetes development induced by streptozocin. Nat Med 1999;5(3):314-319.

Champattanachai, V., et al., Glucosamine protects neonatal cardiomyocytes from ischemia-reperfusion injury via increased protein-associated O-GlcNAc. Am J Physiol Cell Physiol 2007;292(1):C178-187.

Champattanachai, V., et al., Glucosamine protects neonatal cardiomyocytes from ischemia-reperfusion injury via increased protein O-GlcNAc and increased mitochondrial Bcl-2. Am J Physiol Cell Physiol 2008;294(6):C1509-1520.

Cheng, X., et al., Alternative O-glycosylation/O-phosphorylation of the murine estrogen receptor beta. Biochemistry 2000;39(38):11609-11620.

Cheng, X. and Hart, G.W., Alternative O-glycosylation/O-phosphorylation of serine-16 in murine estrogen receptor beta: post-translational regulation of turnover and transactivation activity. J Biol Chem 2001;276(13)10570-10575.

Chou, T.Y. and Hart, G.W., O-linked N-acetylglucosamine and cancer: messages from the glycosylation of c-Myc. Adv Exp Med Biol 2001;491:413-418.

Chou, T.Y. and Hart, G.W., c-Myc is glycosylated at threonine 58, a known phosphorylation site and a mutational hot spot in lymphomas. J Biol Chem 1995;270(32):18961-18965.

Cole, R.N., and Hart, G.W., Glycosylation sites flank phosphorylation sites on synapsin I: O-linked N-acetylglucosamine residues are localized within domains mediating synapsin I interactions. J Neurochem 1999;73(1):418-428.

De La Monte, S.M. and Wands, J.R., Review of insulin and insulin-like growth factor expression, signaling, and malfunction in the central nervous system: relevance to Alzheimer's disease. J Alzheimers Dis 2005;7(1):45-61.

De La Torre, J.C., Alzheimer's disease is a vasocognopathy: a new term to describe its nature. Neurol Res 2004;26(5):517-524.

Deng, Y., et al., Regulation between O-GlcNAcylation and phosphorylation of neurofilament-M and their dysregulation in Alzheimer disease. FASEB J 2008;22(1):138-145.

Dong, D.L. and Hart, G.W., Purification and characterization of an O-GlcNAc selective N-acetyl-beta-D-glucosaminidase from rat spleen cytosol. J Biol Chem 1994;269(30):19321-19330.

Donohoe, T.J. and Rosa, C.P., A concise and efficient synthesis of (−)-allosamizoline. Org Lett 2007;9(26):5509-5511.

Friedhoff, P., et al., Rapid assembly of Alzheimer-like paired helical filaments from microtubule-associated protein tau monitored by fluorescence in solution. Biochemistry 1998;37(28):10223-10230.

Frolich, L., Brain insulin and insulin receptors in aging and sporadic Alzheimer's disease. J Neural Transm 1998;105(4-5):423-438.

Fulop, N., et al., Glucosamine-Induced Cardioprotection Mediated by the Hexosamine Biosynthesis Pathway and Increased Levels of O-Linked N-Acetylglucosamine on Nucleocytoplasmic Proteins. Circulation Research: Abstract Presentations, Jul. 22, 2005;97:e28, Abstract 104.

Fulop, N., et al., Role of protein O-linked N-acetyl-glucosamine in mediating cell function and survival in the cardiovascular system. Cardiovasc Res 2007;73(2):288-297.

Fulop, N., Effects of glucosamine on the isolated rat heart. FASEB J, 2005;19:A689-A690, Abstract #386.6.

Fulop N, et al., 2004 ISHR World Congress Meeting . J Mol Cell Cardiol, Jul. 2004; 37(1):161-375 286.

Gao, Y., et al., Streptozotocin-induced beta-cell death is independent of its inhibition of O-GlcNAcase in pancreatic Min6 cells. Arch Biochem Biophys, 2000;383(2):296-302.

Gao, Y., et al., Dynamic O-glycosylation of nuclear and cytosolic proteins: cloning and characterization of a neutral, cytosolic beta-N-acetylglucosaminidase from human brain. J Biol Chem, 2001; 276(13):9838-9845.

Goedert, M., et al., Tau proteins of Alzheimer paired helical filaments: abnormal phosphorylation of all six brain isoforms. Neuron 1992;8(1):159-168.

Goedert, M., et al., Multiple isoforms of human microtubule-associated protein tau: sequences and localization in neurofibrillary tangles of Alzheimer's disease. Neuron 1989;3(4):519-526.

Goering, B.K. and Ganem, B. Total synthesis of (±)-allosamizoline from a symmetric trisubstituted cyclopentene. Tetrahedron Letters 1994;35(38):6997-7000.

Gong, C.X., et al., Impaired brain glucose metabolism leads to Alzheimer neurofibrillary degeneration through a decrease in tau O-GlcNAcylation. J Alzheimers Dis 2006;9(1):1-12.

Gong C.X., et al., Post-translational modifications of tau protein in Alzheimer's disease. J Neural Transm 2005;112(6):813-38.

Griffith, D.A. and Danishefsky, S.J., The Total Synthesis of Allosamidin. Expansions of the Methodology of Azaglycosylation Pursuant to the Total Synthesis of Allosamidin. A Surprising Enantiotopic Sense for a Lipase-Induced Deacetylation. J Am Chem Soc 1996;118(40):9526-9538.

Griffith, L.S. and Scmitz, B., O-linked N-acetylglucosamine levels in cerebellar neurons respond reciprocally to pertubations of phosphorylation. Eur J Biochem 1999;262(3):824-831.

Haltiwanger, R.S., et al., Modulation of O-linked N-acetylglucosamine levels on nuclear and cytoplasmic proteins in vivo using the peptide O-GlcNAc-beta-N-acetylglucosaminidase inhibitor O-(2-acetamido-2-deoxy-D-glucopyranosylidene) amino-N-phenylcarbamate. J Biol Chem 1998;273(6):3611-3617.

Haltiwanger, R.S., et al., Enzymatic addition of O-GlcNAc to nuclear and cytoplasmic proteins. Identification of a uridine diphospho-N-acetylglucosamine:peptide beta-N-acetylglucosaminyltransferase. J Biol Chem 1990;265(5);2563-2568.

Hanover, J.A., Glycan-dependent signaling: O-linked N-acetylglucosamine. FASEB J 2001;15:1865-1876.

Hanover, J.A., et al., Elevated O-linked N-acetylglucosamine metabolism in pancreatic beta-cells. Arch Biochem Biophys 1999;362(1):38-45.

Henrissat, B. and Bairock, A., New families in the classification of glycosyl hydrolases based on amino acid sequence similarities. Biochem J 1993;293(Pt3):781-788.

Henrissat, B. and Bairock, A., Updating the sequence-based classification of glycosyl hydrolases. Biochem J 1996;316(Pt 2):695-696.

Horsch, M., et al., N-acetylglucosaminono-1,5-lactone oxime and the corresponding (phenylcarbamoyl)oxime. Novel and potent inhibitors of beta-N-acetylglucosaminidase. Eur J Biochem 1991;197(3):815-818.

Hoyer S., Brain glucose and energy metabolism abnormalities in sporadic Alzheimer disease. Causes and consequences: an update. Exp Gerontol 2000;35(9-10):1363-1372.

Hoyer, S., Causes and consequences of disturbances of cerebral glucose metabolism in sporadic Alzheimer disease: Therapeutic Implications. Frontiers in Clinical Neuroscience: Neurodegeneration and Neuroprotection a Symposium in Abel Lajtha's Honour, 2004;541:135-152.

Huang, G.L., et al., Chemo-enzymatic synthesis of tetra-N-acetyl-chitotetraosyl allosamizoline. Bioorg Med Chem Lett 2006;16(11)2860-2861.

Huang, J.B., et al., The hexosamine biosynthesis pathway negatively regulates IL-2 production by Jurkat T cells. Cell Immunol 2007;245(1):1-6.

Iqbal, K., et al., Alzheimer neurofibrillary degeneration: therapeutic targets and high-throughput assays. J Mol Neurosci 2003;20(3);425-459.

Iqbal, K., et al., Pharmacological targets to inhibit Alzheimer neurofibrillary degeneration. Ageing and Dementia Current and Future Concepts: J Neural Transm Suppl 2002;62:309-319.

Iyer, S.P., et al., Identification and cloning of a novel family of coiled-coil domain proteins that interact with O-GlcNAc transferase. J Biol Chem 2003;278(7):5399-53409.

(56) References Cited

OTHER PUBLICATIONS

Iyer, S.P., and Hart, G.W., Roles of the tetratricopeptide repeat domain in O-GlcNAc transferase targeting and protein substrate specificity. J Biol Chem 2003;278(27):24608-24616.
Pickhardt, M., et al., Anthraquinones inhibit tau aggregation and dissolve Alzheimer's paired helical filaments in vitro and in cells. J Biol Chem 2005;280(5):3628-3635.
Roos, M.D., et al., O glycosylation of an Sp1-derived peptide blocks known Sp1 protein interactions. Mol Cell Biol 1997;17(11):6472-6280.
Roos, M.D., et al. Streptozotocin, an analog of N-acetylglucosamine, blocks the removal of O-GlcNAc from intracellular proteins. Proc Assoc Am Physicians 1998;110(5):422-432.
Roquemore, E.P., et al., Dynamic O-GlcNAcylation of the small heat shock protein alpha B-crystallin. Biochemistry 1996;35(11):3578-3586.
Sakuda, S., et al. Absolute Configuration of Allosamizoline, an Aminocyclitol Derivative of the Chitinase Inhibitor Allosamidin. Agric Biol Chem 1988;52(6):1615-1617.
Sakuda, S. et al., Structures of allosamidins, novel insect chitinase inhibitors, produced by actinomycetes. Agric Biol Chem 1987;51(12):3251-3259.
Simpkins, N.S., et al., An enantiospecific synthesis of allosamizoline. J. Chem Soc Perkin Trans 1 1992: 2471-2477.
Simpkins, N.S., et al., An enantiospecific total synthesis of allosamizoline. Tetrahedron Letters 1992;33(6):793-796.
Simpson, I.A., et al., Decreased concentrations of GLUT1 and GLUT3 glucose transporters in the brains of patients with Alzheimer's disease. Ann Neurol 1994;35(5):546-551.
Takahashi, S., et al., Synthesis of a Novel Azapseudodisaccharide related to allosamidin employing N,N'-Diacetylchitobiose as a Key Starting Material. Tetrahedron 1999;55:14871-14884.
Takahashi, S., et al., Stereocontrolled synthesis of (−)-allosamizoline using D-glucosamine as a chiral template. Tetrahedron Letters 1991;32(38):5123-5126.
Takahashi, S., et al., Synthesis of demethylallosamidin, a yeast chitinase inhibitor; use of disaccharide glycosyl donor carrying novel neighboring group. Tetrahedron Letters 1994;35(24):4149-4152.
Toleman, C., et al., Characterization of the histone acetyltransferase (HAT) domain of a bifunctional protein with activable O-GlcNAcase and Hat activities. J Biol Chem 2004;279(51):53665-53673.
Torres, C.R. and Hart, G.W., Topography and polypeptide distribution of terminal N-acetylglucosamine resides on the surfaces of intact lymphocytes. Evidence for O-linked GlcNAc. J Biol Chem 1984;259(5):3308-3317.
Triggs-Raine, B., Naturally occurring mutations in GM2 gangliosidosis: a compendium. Adv Genet 2001;44:199-224.
Trost, B.M., et al., A general synthetic strategy toward aminocyclopentitol glycosidase inhibitors. Application of palladium catalysis to the synthesis of allosamizoline and mannostatin A. J Am Chem Soc 1993;115(2):444-458.
Trost, B.M. and Van Vranken, D.L. Template-directed synthesis of (.+−.)-allosamizoline and its 3,4-epimers. J Am Chem Soc 1990;112(3):1261-1263.
Uchida, C., et al., Synthesis and biological evaluation of potent glycosidase inhibitors: N-phenyl cyclic isourea derivatives of 5-amino- and 5-amino-C-(hydroxymethyl)-1,2,3,4-cyclopentanetetraols. Bioorg Med Chem 1997;5(5):921-939.
Ueno, R. et al., Purification and properties of neutral beta-N-acetylglucosaminidase from carp blood. Biochim Biophys Acta 1991;1074(1):79-84.
Vosseller, K, et al., Elevated nucleocytoplasmic glycosylation by O-GlcNAc results in insulin resistance associated with defects in Akt activation in 3T3-L1 adipocytes. Prac Natl Acad Sci U S A 2002;99(8):5313-5318.
Wakabayashi, T., et al., Preparation of 3,6-di-O-benzylallosamizoline from natural allosamidin. Tetrahedron Asymmetry 2000;11:2083-2091.
Wells, L., et al., O-GlcNAc transferase is in a functional complex with protein phosphatase 1 catalytic subunits. J Biol Chem 2004;279(37):38466-38470.
Wells, L, et la., Glycosylation of nucleocytoplasmic proteins: signal transduction and O-GlcNAc. Science 2001;291(5512):2376-2378.
Yamada, K., et al., Preventive and therapeutic effects of large-dose nicotinamide injections on diabetes associated with insulitis. An observation in nonobese diabetic (NOD) mice. Diabetes 1982;31(9):749-753.
Yamamoto, H., et al., Streptozotocin and alloxan induce DNA strand breaks and poly(ADP-ribose) synthetase in pancreatic islets. Nature 1981;294(5838):284-286.
Yang, S., et al., Glucosamine administration during resuscitation improves organ function after trauma hemorrhage. Shock 2006;25(6):600-607.
Yang, W.H., et al., Modification of p53 with O-linked N-acetylglucosamine regulates p53 activity and stability. Nat Cell Biol 2006;8(10):1074-1083.
Yao, P.J. and Coleman, P.D., Reduction of O-linked N-acetylglucosamine-modified assembly protein-3 in Alzheimer's disease. J Neurosci 1998;18(7):2399-2411.
Yuzwa. S.A., et al., A potent mechanism-inspired O-GlcNAcase inhibitor that blocks phosphorylation of tau in vivo. Nat Chem Biol 2008;4(6):483-490.
Zachara, N.E., et al., Dynamic O-GlcNAc modification of nucleocytoplasmic proteins in response to stress. A survival response of mammalian cells. J Biol Chem 2004;279(29):30133-30142.
Zhang, F., et al., O-GlcNAc modification is an endogenous inhibitor of the proteasome. Cell 2003;115(6):715-725.
Zhou, D., et al., Lysosomal glycosphingolipid recognition by NKT cells. Science 2004;306(5702):1786-1789.
Zhu, X., et al., Insulin signaling, diabetes mellitus and risk of Alzheimer disease. J Alzheimers Dis 2005;7(1):81-84.
Zou, L.Y., et al., Glucosamine improves recovery following trauma hemorrhage in rat. Experimental Biology/IUPS 2005: Meeting Abstracts. FASEB J 2005;19:A1224.
Zou, L.Y., et al., Increasing protein O-GlcNAc levels by inhibition of O-GlcNAcase improves cardiac function following trauma hemorrhage and resuscitation in rat. FASEB J 2006;20:A1471.
Zou, L. et al., The protective effects of PUGNAc on cardiac function after trauma-hemorrhage are mediated via increased protein O-GlcNAc levels. Shock 2007;27(4):402-408.
Office Action issued Jul. 3, 2013 on corresponding Australian Patent Application No. 2009276223.
Search Report issued Oct. 19, 2011 on corresponding European Patent Application No. 09802333.6.
Office Action issued Oct. 10, 2012 on corresponding European Patent Application No. 09802333.6.
English translation of Office Action issued on Jan. 16, 2014 on corresponding Japanese Patent Application No. 2011-520297.
Office Action issued Mar. 25, 2014 on corresponding European Patent Application No. 09802333.6.
Godskesen, M. and Lundt, I., Synthesis and Evaluation of a 5-Membered Isoiminosugar as Glycosidase Inhibitor. Tetrahedron Letters 1998; 39:5841-5844.
Registry entry for CAS Registry for 103766-13-8. Aug. 18, 1986.
Griffith, A.D. and Danishefsky, S.J., Total Synthesis of Allosamidin: An Application of the Sulfonamidoglycosylation of Glycals. J Am Chem Soc 1991; 113:5863-5864.
Griffith, L. S. and Schmitz, B., O-linked N-acetylglucosamine is upregulated in Alzheimer brains. Biochemical Biophysical Research Communications. 1995;213(2): 424-431.
Zachara, N. E, et al., Increased O-GlcNAc in Response to Stress, a Survival Response of Mammals, Joint Meeting of The Society for Glycobiology and The Japanese Society for Carbohydrate Research. Honolulu, HI., Nov. 17-20, 2004 p. 1170, A418.

\* cited by examiner

SELECTIVE GLYCOSIDASE INHIBITORS AND USES THEREOF

This application is a national phase filing under 35 U.S.C. §371 of International Application No. PCT/CA2009/001088, filed on Jul. 31, 2009, which is hereby incorporated by reference in its entirety for all purposes and claims the benefit of and priority to U.S. Provisional Application No. 61/085,538, filed Aug. 1, 2008.

FIELD OF THE INVENTION

This application relates to compounds which selectively inhibit glycosidases and uses thereof.

BACKGROUND OF THE INVENTION

A wide range of cellular proteins, both nuclear and cytoplasmic, are post-translationally modified by the addition of the monosaccharide 2-acetamido-2-deoxy-β-D-glucopyranoside (β-N-acetylglucosamine) which is attached via an O-glycosidic linkage.[1] This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGT).[2-5] A second enzyme, known as O-GlcNAcase[6,7] removes this post-translational modification to liberate proteins making the O-GlcNAc-modification a dynamic cycle occurring several times during the lifetime of a protein.[8]

O-GlcNAc-modified proteins regulate a wide range of vital cellular functions including, for example, transcription,[9-12] proteasomal degradation,[13] and cellular signaling.[14] O-GlcNAc is also found on many structural proteins.[15-17] For example, it has been found on a number of cytoskeletal proteins, including neurofilament proteins,[18,19] synapsins,[6,20] synapsin-specific clathrin assembly protein AP-3,[7] and ankyrinG.[14] O-GlcNAc modification has been found to be abundant in the brain.[21,22] It has also been found on proteins clearly implicated in the etiology of several diseases including Alzheimer's disease (AD) and cancer.

For example, it is well established that AD and a number of related tauopathies including Downs' syndrome, Pick's disease, Niemann-Pick Type C disease, and amyotrophic lateral sclerosis (ALS) are characterized, in part, by the development of neurofibrillary tangles (NFTs). These NFTs are aggregates of paired helical filaments (PHFs) and are composed of an abnormal form of the cytoskeletal protein "tau". Normally tau stabilizes a key cellular network of microtubules that is essential for distributing proteins and nutrients within neurons. In AD patients, however, tau becomes hyperphosphorylated, disrupting its normal functions, forming PHFs and ultimately aggregating to form NFTs. Six isoforms of tau are found in the human brain. In AD patients, all six isoforms of tau are found in NFTs, and all are markedly hyperphosphorylated.[23,24] Tau in healthy brain tissue bears only 2 or 3 phosphate groups, whereas those found in the brains of AD patients bear, on average, 8 phosphate groups.[25,26] A clear parallel between NFT levels in the brains of AD patients and the severity of dementia strongly supports a key role for tau dysfunction in AD.[27,28] The precise causes of this hyperphosphorylation of tau remain elusive. Accordingly, considerable effort has been dedicated toward: a) elucidating the molecular physiological basis of tau hyperphosphorylation;[29] and b) identifying strategies that could limit tau hyperphosphorylation in the hope that these might halt, or even reverse, the progression of Alzheimer's disease[30-33] Thus far, several lines of evidence suggest that up-regulation of a number of kinases may be involved in hyperphosphorylation of tau,[21,34,35] although very recently, an alternative basis for this hyperphosphorylation has been advanced.[21]

In particular, it has recently emerged that phosphate levels of tau are regulated by the levels of O-GlcNAc on tau. The presence of O-GlcNAc on tau has stimulated studies that correlate O-GlcNAc levels with tau phosphorylation levels. The recent interest in this field stems from the observation that O-GlcNAc modification has been found to occur on many proteins at amino acid residues that are also known to be phosphorylated.[36-38] Consistent with this observation, it has been found that increases in phosphorylation levels result in decreased O-GlcNAc levels and conversely, increased O-GlcNAc levels correlate with decreased phosphorylation levels.[39] This reciprocal relationship between O-GlcNAc and phosphorylation has been termed the "Yin-Yang hypothesis"[40] and has gained strong biochemical support by the recent discovery that the enzyme OGT[4] forms a functional complex with phosphatases that act to remove phosphate groups from proteins.[41] Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD.[7,42] Hyperphosphorylated tau in human AD brains has markedly lower levels of O-GlcNAc than are found in healthy human brains.[21] Very recently, it has been shown that O-GlcNAc levels of soluble tau protein from human brains affected with AD are markedly lower than those from healthy brain.[21] Furthermore, PHF from diseased brain was suggested to lack completely any O-GlcNAc modification whatsoever.[21] The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosamindase inhibitor was used to increase tau O-GlcNAc levels, whereupon it was observed that phosphorylation levels decreased.[21] The implication of these collective results is that by maintaining healthy O-GlcNAc levels in AD patients, such as by inhibiting the action of O-GlcNAcase, one should be able to block hyperphosphorylation of tau and all of the associated effects of tau hyperphosphorylation, including the formation of NFTs and downstream effects. However, because the proper functioning of the β-hexosaminidases is critical, any potential therapeutic intervention for the treatment of AD that blocks the action of O-GlcNAcase would have to avoid the concomitant inhibition of both hexosaminidases A and B.

Neurons do not store glucose and therefore the brain relies on glucose supplied by blood to maintain its essential metabolic functions. Notably, it has been shown that within brain, glucose uptake and metabolism decreases with aging.[43] Within the brains of AD patients marked decreases in glucose utilization occur and are thought to be a potential cause of neurodegeneration.[44] The basis for this decreased glucose supply in AD brain[45-47] is thought to stem from any of decreased glucose transport,[48,49] impaired insulin signaling,[50,51] and decreased blood flow.[52]

In light of this impaired glucose metabolism, it is worth noting that of all glucose entering into cells, 2-5% is shunted into the hexosamine biosynthetic pathway, thereby regulating cellular concentrations of the end product of this pathway, uridine diphosphate-N-acetylglucosamine (UDP-GlcNAc).[53] UDP-GlcNAc is a substrate of the nucleocytoplasmic enzyme O-GlcNAc transferase (OGT),[2-5] which acts to post-translationally add GlcNAc to specific serine and threonine residues of numerous nucleocytoplasmic proteins. OGT recognizes many of its substrates[54,55] and binding partners[41,56] through its tetratricopeptide repeat (TPR) domains.[57,58] As described above, O-GlcNAcase[6,7] removes this post-translational modification to liberate proteins making the O-GlcNAc-modification a dynamic cycle occurring several times during the lifetime of a protein.[8] O-GlcNAc has been found in several proteins on known phosphorylation sites,[10,37,38,59] including tau and neurofilaments.[60] Additionally, OGT shows unusual kin behaviour making it exquisitely sensitive to intracellular UDP-GlcNAc substrate concentrations and therefore glucose supply.[41]

Consistent with the known properties of the hexosamine biosynthetic pathway, the enzymatic properties of OGT, and the reciprocal relationship between O-GlcNAc and phosphorylation, it has been shown that decreased glucose availability in brain leads to tau hyperphosphorylation.[44] Therefore the gradual impairment of glucose transport and metabolism, whatever its causes, leads to decreased O-GlcNAc and hyperphosphorylation of tau (and other proteins). Accordingly, the inhibition of O-GlcNAcase should compensate for the age related impairment of glucose metabolism within the brains of health individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention[61] comes from recent studies showing that when transgenic mice harbouring human tau are treated with kinase inhibitors, they do not develop typical motor defects[33] and, in another case,[32] show decreased levels of insoluble tau. These studies provide a clear link between lowering tau phosphorylation levels and alleviating AD-like behavioural symptoms in a murine model of this disease. Indeed, pharmacological modulation of tau hyperphosphorylation is widely recognized as a valid therapeutic strategy for treating AD and other neurodegenerative disorders.[62]

Recent studies[63] support the therapeutic potential of small-molecule O-GlcNAcase inhibitors to limit tau hyperphosphorylation for treatment of AD and related tauopathies. Specifically, the O-GlcNAcase inhibitor thiamet-G has been implicated in the reduction of tau phosphorylation in cultured PC-12 cells at pathologically relevant sites.[63] Moreover, oral administration of thiamet-G to healthy Sprague-Dawley rats has been implicated in reduced phosphorylation of tau at Thr231, Ser396 and Ser422 in both rat cortex and hippocampus.[63]

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animals models of ischemia/reperfusion[64-70] trauma hemorrhage,[71-73] hypervolemic shock,[74] and calcium paradox.[64,75] Moreover, strong evidence indicates that these cardioprotective effects are mediated by elevated levels of protein O-GlcNAc modification.[64,65,67,70,72,75-78] There is also evidence that the O-GlcNAc modification plays a role in a variety of neurodegenerative diseases, including Parkinson's disease and Huntington's disease.[79]

Humans have three genes encoding enzymes that cleave terminal β-N-acetyl-glucosamine residues from glycoconjugates. The first of these encodes the enzyme O-glycoprotein 2-acetamido-2-deoxy-β-D-glucopyranosidase (O-GlcNAcase). O-GlcNAcase is a member of family 84 of glycoside hydrolases that includes enzymes from organisms as diverse as prokaryotic pathogens to humans (for the family classification of glycoside hydrolases see Coutinho, P. M. & Henrissat, B. (1999) Carbohydrate-Active Enzymes server at URL: http://afmb.cnrs-mrs.fr/CAZY/.[27,28] O-GlcNAcase acts to hydrolyse O-GlcNAc off of serine and threonine residues of post-translationally modified proteins.[1,6,7,80,81] Consistent with the presence of O-GlcNAc on many intracellular proteins, the enzyme O-GlcNAcase appears to have a role in the etiology of several diseases including type II diabetes,[14,82] AD[16,21,83] and cancer.[22,84] Although O-GlcNAcase was likely isolated earlier on,[18,19] about 20 years elapsed before its biochemical role in acting to cleave O-GlcNAc from serine and threonine residues of proteins was understood.[6] More recently O-GlcNAcase has been cloned,[7] partially characterized,[20] and suggested to have additional activity as a histone acetyltransferase.[20] However, little was known about the catalytic mechanism of this enzyme.

The other two genes, HEXA and HEXB, encode enzymes catalyzing the hydrolytic cleavage of terminal β-N-acetylglucosamine residues from glycoconjugates. The gene products of HEXA and HEXB predominantly yield two dimeric isozymes, hexosaminidase A and hexosaminidase B, respectively. Hexosaminidase A ($\alpha\beta$), a heterodimeric isozyme, is composed of an $\alpha$- and a $\beta$-subunit. Hexosaminidase B ($\beta\beta$), a homodimeric isozyme, is composed of two $\beta$-subunits. The two subunits, $\alpha$- and $\beta$-, bear a high level of sequence identity. Both of these enzymes are classified as members of family 20 of glycoside hydrolases and are normally localized within lysosomes. The proper functioning of these lysosomal β-hexosaminidases is critical for human development, a fact that is underscored by the tragic genetic illnesses, Tay-Sach's and Sandhoff diseases which stem from a dysfunction in, respectively, hexosaminidase A and hexosaminidase B.[85] These enzymatic deficiencies cause an accumulation of glycolipids and glycoconjugates in the lysosomes resulting in neurological impairment and deformation. The deleterious effects of accumulation of gangliosides at the organismal level are still being uncovered.[86]

As a result of the biological importance of these β-N-acetyl-glucosaminidases, small molecule inhibitors of glycosidases[87-90] have received a great deal of attention,[91] both as tools for elucidating the role of these enzymes in biological processes and in developing potential therapeutic applications. The control of glycosidase function using small molecules offers several advantages over genetic knockout studies including the ability to rapidly vary doses or to entirely withdraw treatment.

However, a major challenge in developing inhibitors for blocking the function of mammalian glycosidases, including O-GlthAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, existing compounds that act to block O-GlcNAcase function are non-specific and act potently to inhibit the lysosomal β-hexosaminidases.

A few of the better characterized inhibitors of β-N-acetyl-glucosaminidases which have been used in studies of O-GlcNAc post-translational modification within both cells and tissues are streptozotocin (STZ), 2'-methyl-α-D-glucopyrano-[2,1-d]-Δ2'-thiazoline (NAG-thiazoline) and O-(2-acetamido-2-deoxy-D-glucopyranosylidene)amino N-phenylcarbamate (PUGNAc).[14,92-95]

STZ has long been used as a diabetogenic compound because it has a particularly detrimental effect on β-islet cells.[96] STZ exerts its cytotoxic effects through both the alkylation of cellular DNA[96,97] as well as the generation of radical species including nitric oxide.[98] The resulting DNA strand breakage promotes the activation of poly(ADP-ribose) polymerase (PARP)[99] with the net effect of depleting cellular NAD+ levels and, ultimately, leading to cell death.[100,101] Other investigators have proposed instead that STZ toxicity is a consequence of the irreversible inhibition of O-GlcNAcase, which is highly expressed within β-islet cells.[92,102] This hypothesis has, however, been brought into question by two independent research groups.[103,104] Because cellular O-GlcNAc levels on proteins increase in response to many forms of cellular stress[105] it seems possible that STZ results in increased O-GlcNAc-modification levels on proteins by inducing cellular stress rather than through any specific and direct action on O-GlcNAcase. Indeed, Hanover and coworkers have shown that STZ functions as a poor and somewhat selective inhibitor of O-GlcNAcase[106] and although it has been proposed by others that STZ acts to irreversibly inhibit O-GlcNAcase,[107] there has been no clear demonstration of this mode of action. Recently, it has been shown that STZ does not irreversibly inhibit O-GlcNAcase.[108]

NAG-thiazoline has been found to be a potent inhibitor of family 20 hexosaminidases,[90,109] and more recently, the family 84 O-GlcNAcases.[108] Despite its potency, a downside to using NAG-thiazoline in a complex biological context is that it lacks selectivity and therefore perturbs multiple cellular processes.

PUGNAc is another compound that suffers from the same problem of lack of selectivity, yet has enjoyed use as an inhibitor of both human O-GlcNAcase[6,110] and the family 20 human β-hexosaminidases.[111] This molecule, developed by Vasella and coworkers, was found to be a potent competitive inhibitor of the β-N-acetyl-glucosaminidases from *Canavalia ensiformis, Mucor rouxii*, and the β-hexosaminidase from bovine kidney.[88] It has been demonstrated that administration of PUGNAc in a rat model of trauma hemorrhage decreases circulating levels of the pro-inflammatory cytokines TNF-α and IL-6.[112] It has also been shown that administration of PUGNAc in a cell-based model of lymphocyte activation decreases production of the cytokine IL-2.[113] Recent studies have indicated that PUGNAc can be used in an animal model to reduce myocardial infarct size after left coronary artery occlusions.[114] Of particular significance is the fact that elevation of O-GlcNAc levels by administration of PUGNAc, an inhibitor of O-GlcNAcase, in a rat model of trauma hemorrhage improves cardiac function.[112,115] In addition, elevation of O-GlcNAc levels by treatment with PUGNAc in a cellular model of ischemia/reperfusion injury using neonatal rat ventricular myocytes improved cell viability and reduced necrosis and apoptosis compared to untreated cells.[116]

More recently, it has been suggested that the selective O-GlcNAcase inhibitor NButGT exhibits protective activity in cell-based models of ischemia/reperfusion and cellular stresses, including oxidative stress.[117] This evidence suggests the use of O-GlcNAcase inhibitors to elevate protein O-GlcNAc levels and thereby prevent the pathogenic effects of stress in cardiac tissue.

International patent applications PCT/CA2006/000300, filed 1 Mar. 2006, published under No. WO 2006/092049 on 8 Sep. 2006, and PCT/CA2007/001554, filed 31 Aug. 2007, published under No. WO 2008/025170 on 6 Mar. 2008, which are hereby incorporated by reference, describe selective inhibitors of O-GlcNAcase

SUMMARY OF THE INVENTION

The invention provides, in part, compounds for selectively inhibiting glycosidases, prodrugs of the compounds, uses of the compounds and the prodrugs, pharmaceutical compositions including the compounds or prodrugs of the compounds, and methods of treating diseases and disorders related to deficiency or overexpression of O-GlcNAcase, and/or accumulation or deficiency of O-GlcNAc.

In one aspect, the invention provides a compound of Formula (I) or a pharmaceutically acceptable salt thereof:

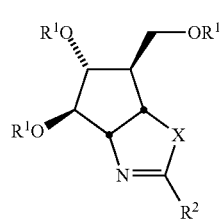

(I)

where each $R^1$ may be independently a non-interfering substituent; X may be O, S, or $NR^3$; $R^2$ is $NR^3{}_2$; where each $R^3$ may be optionally independently a non-interfering substituent, with the proviso that when X is O and each $R^1$ is H or $C(O)CH_3$, $R^2$ excludes $N(CH_3)_2$.

In alternative embodiments, each $R^1$ may be connected to another $R^1$ to form an additional ring structure.

In alternative embodiments, the non-interfering substituent may be alkyl, alkenyl, alkynyl, aryl, arylalkyl, arylalkenyl, or arylalkynyl, or may include one or more heteroatoms selected from P, O, S, N, F, Cl, Br, I, or B. The non-interfering substituent may be optionally substituted.

In alternative embodiments, the compound may be a prodrug; the compound may selectively inhibit an O-glycoprotein 2-acetamido-2-deoxy-β-D-glucopyranosidase (O-GlcNAcase); the compound may selectively bind an O-GlcNAcase (e.g., a mammalian O-GlcNAcase); the compound may selectively inhibit the cleavage of a 2-acetamido-2-deoxy-β-D-glucopyranoside (O-GlcNAc); the compound may not substantially inhibit a mammalian β-hexosaminidase.

In alternative aspects, the invention provides a pharmaceutical composition including a compound according to the invention, in combination with a pharmaceutically acceptable carrier.

In alternative aspects, the invention provides methods of selectively inhibiting an O-GlcNAcase, or of inhibiting an O-GlcNAcase in a subject in need thereof, or of increasing the level of O-GlcNAc, or of treating a neurodegenerative disease, a tauopathy, cancer or stress, in a subject in need thereof, by administering to the subject an effective amount of a compound of Formula (I) or a pharmaceutically acceptable salt thereof:

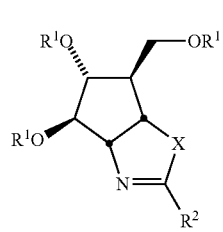

(I)

wherein each $R^1$ may be independently a non-interfering substituent; X may be O, S, or $NR^3$; $R^2$ may be $NR^3{}_2$; where each $R^3$ may be optionally independently a non-interfering substituent. The condition may be Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, Huntington's disease, or Parkinson's disease. The stress may be a cardiac disorder, e.g., ischemia; hemorrhage; hypovolemic shock; myocardial infarction; an interventional cardiology procedure; cardiac bypass surgery; fibrinolytic therapy; angioplasty; or stent placement.

In alternative aspects, the invention provides a method of treating an O-GlcNAcase-mediated condition that excludes a neurodegenerative disease, a tauopathy, cancer or stress, in a subject in need thereof, by administering to the subject an effective amount of a compound of Formula (I) or a pharmaceutically acceptable salt thereof:

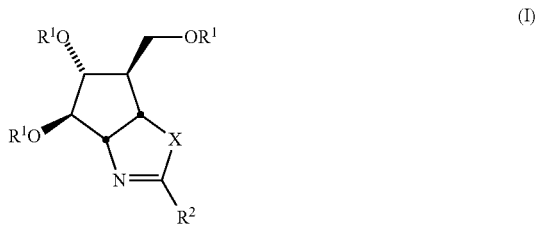

(I)

wherein each $R^1$ may be independently a non-interfering substituent; X may be O, S, or $NR^3$; $R^2$ may be $NR^3{}_2$; where each $R^3$ may be optionally independently a non-interfering substituent. In some embodiments, the condition may be inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, systemic lupus erythematosus, myastenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, and eosiniphilic fasciitis; graft rejection, in particular but not limited to solid organ transplants, such as heart, lung, liver, kidney, and pancreas transplants (e.g. kidney and lung allografts); epilepsy; pain; stroke, e.g., neuroprotection following a stroke.

In alternative embodiments, X may be O; $R^1$ may be H or $C(O)CH_3$. The administering may increase the level of O-GlcNAc in the subject. The subject may be a human.

In alternative aspects, the invention provides use of a compound of an effective amount of a compound of Formula (I) or a pharmaceutically acceptable salt thereof:

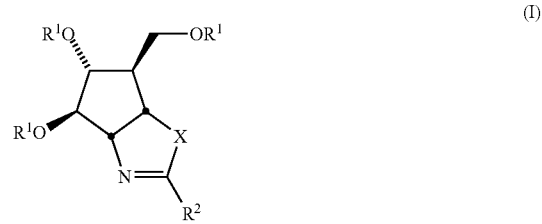

(I)

where each $R^1$ may be independently a non-interfering substituent; X may be O, S, or $NR^3$; $R^2$ may be $NR^3{}_2$; where each $R^3$ may be optionally independently a non-interfering substituent, in the preparation of a medicament. The medicament may be for selectively inhibiting an O-GlcNAcase, for increasing the level of O-GlcNAc, for treating a condition modulated by an O-GlcNAcase, for treating a neurodegenerative disease, a tauopathy, a cancer, or stress.

In alternative aspects, the invention provides a method for screening for a selective inhibitor of an O-GlcNAcase, by a) contacting a first sample with a test compound; b) contacting a second sample with a compound of Formula (I)

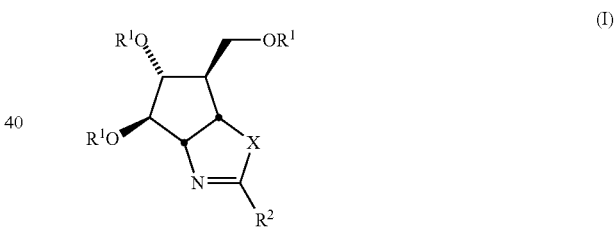

(I)

where each $R^1$ may be independently a non-interfering substituent; X may be O, S, or $NR^3$; $R^2$ may be $NR^3{}_2$; where each $R^3$ may be optionally independently a non-interfering substituent, c) determining the level of inhibition of the O-GlcNAcase in the first and second samples, where the test compound is a selective inhibitor of a O-GlcNAcase if the test compound exhibits the same or greater inhibition of the O-GlcNAcase when compared to the compound of Formula (I).

This summary of the invention does not necessarily describe all features of the invention.

DETAILED DESCRIPTION

The invention provides, in part, novel compounds that are capable of inhibiting an O-glycoprotein 2-acetamido-2-deoxy-β-D-glucopyranosidase (O-GlcNAcase). In some embodiments, the O-GlcNAcase is a mammalian O-GlcNAcase, such as a rat, mouse or human O-GlcNAcase. In some embodiments, the β-hexosaminidase is a mammalian β-hexosaminidase, such as a rat, mouse or human β-hexosaminidase.

In some embodiments, compounds according to the invention exhibit a surprising and unexpected selectivity in inhibiting an O-GlcNAcase. In some embodiments, the compounds according to the invention are surprisingly more selective for an O-GlcNAcase over a β-hexosaminidase. In some embodiments, the compounds selectively inhibit the activity of a mammalian O-GlcNAcase over a mammalian β-hexosaminidase. In some embodiments, a selective inhibitor of an O-GlcNAcase does not substantially inhibit a β-hexosaminidase. A compound that "selectively" inhibits an O-GlcNAcase is a compound that inhibits the activity or biological function of an O-GlcNAcase, but does not substantially inhibit the activity or biological function of a β-hexosaminidase. For example, in some embodiments, a selective inhibitor of an O-GlcNAcase selectively inhibits the cleavage of 2-acetamido-2-deoxy-β-D-glucopyranoside (O-GlcNAc) from polypeptides. In some embodiments, a selective inhibitor of an O-GlcNAcase selectively binds to an O-GlcNAcase. In some embodiments, a selective inhibitor of an O-GlcNAcase inhibits hyperphosphorylation of a tau protein and/or inhibits formations of NFTs. By "inhibits," "inhibition" or "inhibiting" means a decrease by any value between 10% and 90%, or of any integer value between 30% and 60%, or over 100%, or a decrease by 1-fold, 2-fold, 5-fold, 10-fold or more. It is to be understood that the inhibiting does not require full inhibition. In some embodiments, a selective inhibitor of an O-GlcNAcase elevates or enhances O-GlcNAc levels e.g., O-GlcNAc-modified polypeptide or protein levels, in cells, tissues, or organs (e.g., in brain, muscle, or heart (cardiac) tissue) and in animals. By "elevating" or "enhancing" is meant an increase by any value between 10% and 90%, or of any integer value between 30% and 60%, or over 100%, or an increase by 1-fold, 2-fold, 5-fold, 10-fold, 15-fold, 25-fold, 50-fold, 100-fold or more. In some embodiments, a selective inhibitor of an O-GlcNAcase exhibits a selectivity ratio, as described herein, in the range 100 to 100000, or in the range 1000 to 100000, or at least 100, 200, 500, 1000, 1500, 2000, 2500, 3000, 3500, 4000, 4500, 5000, 6000, 7000, 10,000, 25,000, 50,000, 75,000, or any value within or about the described range.

The compounds of the present invention elevate O-GlcNAc levels on O-GlcNAc-modified polypeptides or proteins in vivo specifically via interaction with an O-GlcNAcase enzyme, and are effective in treating conditions which require or respond to inhibition of O-GlcNAcase activity.

In some embodiments, the compounds of the present invention are useful as agents that produce a decrease in tau phosphorylation and NFT formation. In some embodiments, the compounds are therefore useful to treat Alzheimer's disease and related tauopathies. In some embodiments, the compounds are thus capable of treating Alzheimer's disease and related tauopathies by lowering tau phosphorylation and reducing NFT formation as a result of increasing tau O-GlcNAc levels. In some embodiments, the compounds produce an increase in levels of O-GlcNAc modification on O-GlcNAc-modified polypeptides or proteins, and are therefore useful for treatment of disorders responsive to such increases in O-GlcNAc modification; these disorders include without limitation neurodegenerative, inflammatory, cardiovascular, and immunoregulatory diseases. In some embodiments, the compounds are also useful as a result of other biological activities related to their ability to inhibit the activity of glycosidase enzymes. In alternative embodiments, the compounds of the invention are valuable tools in studying the physiological role of O-GlcNAc at the cellular and organismal level.

In alternative embodiments, the invention provides methods of enhancing or elevating levels of protein O-GlcNAc modification in animal subjects, such as, veterinary and human subjects. In alternative embodiments, the invention provides methods of selectively inhibiting an O-GlcNAcase enzyme in animal subjects, such as, veterinary and human subjects. In alternative embodiments, the invention provides methods of inhibiting phosphorylation of tau polypeptides, or inhibiting formation of NFTs, in animal subjects, such as, veterinary and human subjects.

In specific embodiments, the invention provides compounds described generally by Formula (I) and the salts, prodrugs, and stereoisomeric forms thereof:

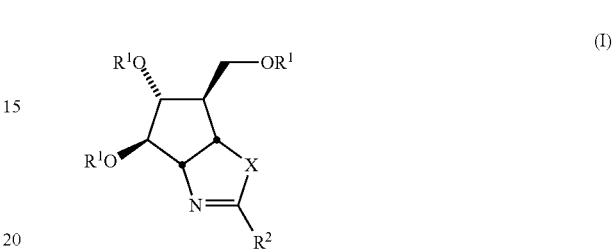

(I)

As set forth in Formula (I): each $R^1$ can be independently a non-interfering substituent; X can be O, S, or $NR^3$; $R^2$ can be $NR^3_2$, where each $R^3$ may be optionally independently a non-interfering substituent. In some embodiments, each $R^1$ may be connected to another $R^1$ to form an additional ring structure.

In the above Formula (I), each optionally substituted moiety may be substituted with one or more non-interfering substituents. For example, each optionally substituted moiety may be substituted with one or more inorganic substituents; phosphoryl; halo; =O; $=NR^4$; OR; $C_{1-10}$ alkyl or $C_{2-10}$ alkenyl optionally containing one or more P, N, O, S, N, F, Cl, Br, I, or B, and optionally substituted with halo; CN; optionally substituted carbonyl; $NR^4_2$; $C=NR^4$; an optionally substituted carbocyclic or heterocyclic ring; or an optionally substituted aryl or heteroaryl. $R^4$ may be alkyl, branched alkyl, cycloalkyl, aryl, or heteroaryl.

In some embodiments, $R^1$ as set forth in Formula (I), may be either hydrogen or a substituent that includes 1-20 atoms that are other than hydrogen. In some embodiments, $R^1$ may be H, alkyl, or $C(O)R^4$, where $R^4$ may be alkyl, branched alkyl, cycloalkyl, aryl, or heteroaryl. In some embodiments, $R^1$ may be H or $C(O)CH_3$.

In some embodiments, $R^2$ as set forth in Formula (I), may be optionally substituted $NR^5_2$, where $R^5$ may be H, alkyl, branched alkyl, cycloalkyl, aryl, or heteroaryl. In some embodiments, $R^2$ may be $N(CH_3)_2$.

In specific embodiments of the invention, compounds according to Formula (I) include the compounds described in Table 1.

TABLE 1

| Compound | Name | Structure |
|---|---|---|
| 1 | (3aS,4R,5R,6S,6aS)-6-(acetoxymethyl)-2-(dimethylamino)-4,5,6,6a-tetrahydro-3aH-cyclopenta[d]oxazole-4,5-diyl diacetate | 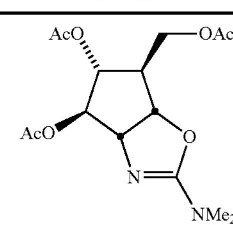 |

TABLE 1-continued

| Compound | Name | Structure |
|---|---|---|
| 2 | (3aR,4R,5R,6R,6aS)-2-(dimethylamino)-6-(hydroxymethyl)-4,5,6,6a-tetrahydro-3aH-cyclopenta[d]oxazole-4,5-diol | 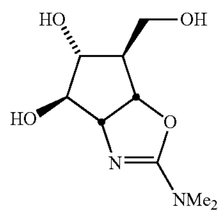 [SMILES: CN(C)C1=N[C@@H]2[C@@H](O)[C@H](O)[C@@H](CO)[C@@H]2O1] |

In alternative embodiments of the invention, compounds according to Formula (I) include one or more of the compounds described in Table 2.

TABLE 2

| Compound | Name | Structure |
|---|---|---|
| 3 | (3aR,4R,5R,6R,6aS)-2-amino-6-(hydroxymethyl)-4,5,6,6a-tetrahydro-3aH-cyclopenta[d]oxazole-4,5-diol | 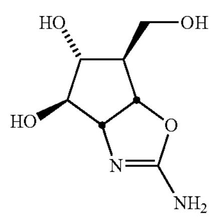 [SMILES: NC1=N[C@@H]2[C@@H](O)[C@H](O)[C@@H](CO)[C@@H]2O1] |
| 4 | (3aR,4R,5R,6R,6aS)-6-(hydroxymethyl)-2-(methylamino)-4,5,6,6a-tetrahydro-3aH-cyclopenta[d]oxazole-4,5-diol | 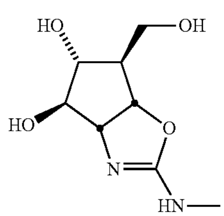 |
| 5 | (3aR,4R,5R,6R,6aS)-2-(ethylamino)-6-(hydroxymethyl)-4,5,6,6a-tetrahydro-3aH-cyclopenta[d]oxazole-4,5-diol | 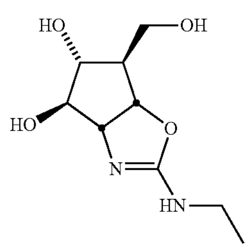 |
| 6 | (3aR,4R,5R,6R,6aS)-6-(hydroxymethyl)-2-(propylamino)-4,5,6,6a-tetrahydro-3aH-cyclopenta[d]oxazole-4,5-diol | 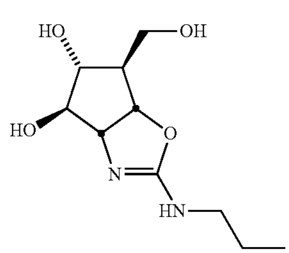 [SMILES: CCCNC1=N[C@@H]2[C@@H](O)[C@H](O)[C@@H](CO)[C@@H]2O1] |

TABLE 2-continued

| Compound | Name | Structure |
|---|---|---|
| 7 | (3aR,4R,5R,6R,6aR)-2-(butylamino)-6-(hydroxymethyl)-4,5,6,6a-tetrahydro-3aH-cyclopenta[d]oxazole-4,5-diol | 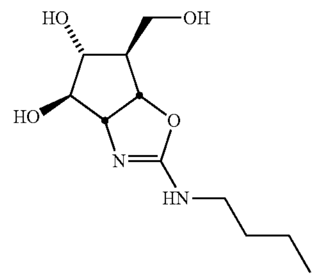 [SMILES: CCCCNC1=N[C@@H]2[C@@H](O)[C@H](O)[C@@H](CO)[C@@H]2O1] |
| 8 | (3aR,4R,5R,6R,6aS)-2-(allylamino)-6-(hydroxymethyl)-4,5,6,6a-tetrahydro-3aH-cyclopenta[d]oxazole-4,5-diol | 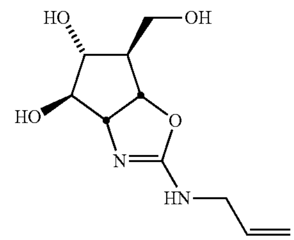 [SMILES: C=CCNC1=N[C@@H]2[C@@H](O)[C@H](O)[C@@H](CO)[C@@H]2O1] |
| 9 | (3aR,4R,5R,6R,6aS)-2-(ethyl(methyl)amino)-6-(hydroxymethyl)-4,5,6,6a-tetrahydro-3aH-cyclopenta[d]oxazole-4,5-diol | 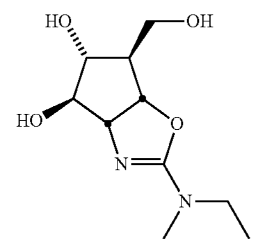 [SMILES: CCN(C)C1=N[C@@H]2[C@@H](O)[C@H](O)[C@@H](CO)[C@@H]2O1] |
| 10 | (3aR,4R,5R,6R,6aS)-2-(diethylamino)-6-(hydroxymethyl)-4,5,6,6a-tetrahydro-3aH-cyclopenta[d]oxazole-4,5-diol | 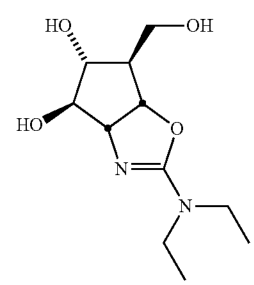 [SMILES: CCN(CC)C1=N[C@@H]2[C@@H](O)[C@H](O)[C@@H](CO)[C@@H]2O1] |
| 11 | (3aR,4R,5R,6R,6aS)-6-(hydroxymethyl)-2-(pyrrolidin-1-yl)-4,5,6,6a-tetrahydro-3aH-cyclopenta[d]oxazole-4,5-diol | 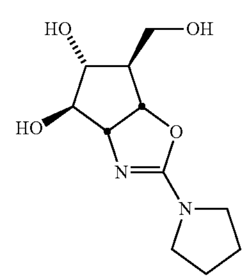 [SMILES: OC[C@@H]1[C@@H](O)[C@H](O)[C@H]2N=C(N3CCCC3)O[C@@H]12] |
| 12 | (3aR,4R,5R,6R,6aS)-2-amino-6-(hydroxymethyl)-4,5,6,6a-tetrahydro-3aH-cyclopenta[d]thiazole-4,5-diol | 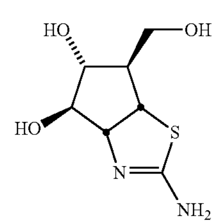 [SMILES: NC1=N[C@@H]2[C@@H](O)[C@H](O)[C@@H](CO)[C@@H]2S1] |

TABLE 2-continued

| Compound Name | Structure |
|---|---|
| 13 (3aR,4R,5R,6R,6aS)-6-(hydroxymethyl)-2-(methylamino)-4,5,6,6a-tetrahydro-3aH-cyclopenta[d]thiazole-4,5-diol | |
| 14 (3aR,4R,5R,6R,6aS)-2-(ethylamino)-6-(hydroxymethyl)-4,5,6,6a-tetrahydro-3aH-cyclopenta[d]thiazole-4,5-diol | |
| 15 (3aR,4R,5R,6R,6aS)-6-(hydroxymethyl)-2-(propylamino)-4,5,6,6a-tetrahydro-3aH-cyclopenta[d]thiazole-4,5-diol | |
| 16 (3aR,4R,5R,6R,6aS)-2-(butylamino)-6-(hydroxymethyl)-4,5,6,6a-tetrahydro-3aH-cyclopenta[d]thiazole-4,5-diol | |
| 17 (3aR,4R,5R,6R,6aS)-2-(allylamino)-6-(hydroxymethyl)-4,5,6,6a-tetrahydro-3aH-cyclopenta[d]thiazole-4,5-diol | |
| 18 (3aR,4R,5R,6R,6aR)-2-(dimethylamino)-6-(hydroxymethyl)-4,5,6,6a-tetrahydro-3aH-cyclopenta[d]thiazole-4,5-diol | |
| 19 (3aR,4R,5R,6R,6aS)-2-(ethyl(methyl)amino)-6-(hydroxymethyl)-4,5,6,6a-tetrahydro-3aH-cyclopenta[d]thiazole-4,5-diol | |
| 20 (3aR,4R,5R,6R,6aS)-2-(diethylamino)-6-(hydroxymethyl)-4,5,6,6a-tetrahydro-3aH-cyclopenta[d]thiazole-4,5-diol | |
| 21 (3aR,4R,5R,6R,6aS)-6-(hydroxymethyl)-2-(pyrrolidin-1-yl)-4,5,6,6a-tetrahydro-3aH-cyclopenta[d]thiazole-4,5-diol | |

In alternative embodiments of the invention, one or more of the compounds described in Table 1 are specifically excluded from the compounds described in Formula (I). In alternative embodiments of the invention, specific stereoisomers or enantiomers of one or more of the compounds described in Table 1 are specifically excluded from the compounds described in Formula (I). In alternative embodiments of the invention, specific precursors of one or more of the compounds described in Table 1 are specifically excluded from the compounds described in Formula (I).

In alternative embodiments, when X is O and each $R^1$ is H or $C(O)CH_3$, $R^2$ excludes $N(CH_3)_2$.

As will be appreciated by a person skilled in the art, Formula (I) above may also be represented alternatively as follows:

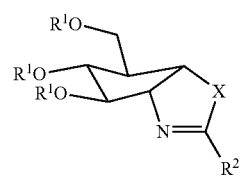

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Throughout this application, it is contemplated that the term "compound" or "compounds" refers to the compounds discussed herein and includes precursors and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

In some embodiments, all of the compounds of the invention contain at least one chiral center. In some embodiments, the formulations, preparation, and compositions including compounds according to the invention include mixtures of stereoisomers, individual stereoisomers, and enantiomeric mixtures, and mixtures of multiple stereoisomers. In general, the compound may be supplied in any desired degree of chiral purity.

In general, a "non-interfering substituent" is a substituent whose presence does not destroy the ability of the compound of Formula (I) to modulate the activity of the O-GlcNAcase enzyme. Specifically, the presence of the substituent does not destroy the effectiveness of the compound as a modulator of the activity of the O-GlcNAcase enzyme.

Suitable non-interfering substituents include: H, alkyl ($C_{1-10}$, alkenyl ($C_{2-10}$, alkynyl ($C_{2-10}$), aryl (5-12 members), arylalkyl, arylalkenyl, or arylalkynyl, each of which may optionally contain one or more heteroatoms selected from O, S, P, N, F, Cl, Br, I, or B, and each of which may be further substituted, for example, by =O; or optionally substituted forms of acyl, arylacyl, alkyl- alkenyl-, alkynyl- or arylsulfonyl and forms thereof which contain heteroatoms in the alkyl, alkenyl, alkynyl or aryl moieties. Other noninterfering substituents include =O, =NR, halo, CN, $CF_3$, $CHF_2$, $NO_2$, OR, SR, $NR_2$, $N_3$, COOR, and $CONR_2$, where R is H or alkyl, cycloalkyl, alkenyl, alkynyl, aryl, or heteroaryl. Where the substituted atom is C, the substituents may include, in addition to the substituents listed above, halo, OOCR, NROCR, where R is H or a substituent set forth above.

"Alkyl" refers to a straight or branched hydrocarbon chain group consisting solely of carbon and hydrogen atoms, containing no unsaturation and including, for example, from one to ten carbon atoms, and which is attached to the rest of the molecule by a single bond. Unless stated otherwise specifically in the specification, the alkyl group may be optionally substituted by one or more substituents as described herein. Unless stated otherwise specifically herein, it is understood that the substitution can occur on any carbon of the alkyl group.

"Alkenyl" refers to a straight or branched hydrocarbon chain group consisting solely of carbon and hydrogen atoms, containing at least one double bond and including, for example, from two to ten carbon atoms, and which is attached to the rest of the molecule by a single bond or a double bond. Unless stated otherwise specifically in the specification, the alkenyl group may be optionally substituted by one or more substituents as described herein. Unless stated otherwise specifically herein, it is understood that the substitution can occur on any carbon of the alkenyl group.

"Alkynyl" refers to a straight or branched hydrocarbon chain group consisting solely of carbon and hydrogen atoms, containing at least one triple bond and including, for example, from two to ten carbon atoms. Unless stated otherwise specifically in the specification, the alkenyl group may be optionally substituted by one or more substituents as described herein.

"Aryl" refers to a phenyl or naphthyl group, including for example, 5-12 members. Unless stated otherwise specifically herein, the term "aryl" is meant to include aryl groups optionally substituted by one or more substituents as described herein.

"Arylalkyl" refers to a group of the formula —$R_aR_b$ where $R_a$ is an alkyl group as described herein and $R_b$ is one or more aryl moieties as described herein. The aryl group(s) may be optionally substituted as described herein.

"Arylalkenyl" refers to a group of the formula —$R_cR_b$ where $R_c$ is an alkenyl moiety as described herein and $R_b$ is one or more aryl groups as described herein. The aryl group(s) and the alkenyl group may be optionally substituted as described herein.

"Acyl" refers to a group of the formula —C(O)$R_a$, where $R_a$ is an alkyl group as described herein. The alkyl group(s) may be optionally substituted as described herein.

"Arylacyl" refers to a group of the formula —C(O)$R_b$, where $R_b$ is an aryl group as described herein. The aryl group(s) may be optionally substituted as described herein.

"Cycloalkyl" refers to a stable monovalent monocyclic, bicyclic or tricyclic hydrocarbon group consisting solely of carbon and hydrogen atoms, having for example from 3 to 15 carbon atoms, and which is saturated and attached to the rest of the molecule by a single bond. Unless otherwise stated specifically herein, the term "cycloalkyl" is meant to include cycloalkyl groups which are optionally substituted as described herein.

By a "ring structure" is meant a cycloalkyl, aryl, heteroaryl, or any cyclic structure that may be optionally substituted.

"Optional" or "optionally" means that the subsequently described event of circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution. Examples of optionally substituted alkyl groups include, without limitation, methyl, ethyl, propyl, etc. and including cycloalkyls such as cyclopropyl, cyclobutyl, cyclopentyl, cyclohexyl, cycloheptyl, etc.; examples of optionally substituted alkenyl groups include allyl, crotyl, 2-pentenyl, 3-hexenyl, 2-cyclopentenyl, 2-cyclohexenyl, 2-cyclopentenylmethyl, 2-cyclohexenylmethyl, etc. In some embodiments, optionally substituted alkyl and alkenyl groups include $C_{1-6}$ alkyls or alkenyls.

"Halo" refers to bromo, chloro, fluoro, iodo, etc. In some embodiments, suitable halogens include fluorine or chlorine.

An amino group may also be substituted once or twice (to form a secondary or tertiary amine) with a group such as an optionally substituted alkyl group including $C_{1-10}$alkyl (e.g., methyl, ethyl propyl etc.); an optionally substituted alkenyl group such as allyl, crotyl, 2-pentenyl, 3-hexenyl, etc., or an optionally substituted cycloalkyl group such as cyclopropyl, cyclobutyl, cyclopentyl, cyclohexyl, cycloheptyl, etc. In these cases, $C_{1-6}$ alkyl, alkenyl and cycloalkyl are preferred. The amine group may also be optionally substituted with an aromatic or heterocyclic group, aralkyl (e.g., phenyl$C_{1-4}$ alkyl) or heteroalkyl for example, phenyl, pyridine, phenylmethyl (benzyl), phenethyl, pyridinylmethyl, pyridinylethyl, etc. The heterocyclic group may be a 5 or 6 membered ring containing 1-4 heteroatoms.

An amino group may be substituted with an optionally substituted $C_{2-4}$ alkanoyl, e.g., acetyl, propionyl, butyryl, isobutyryl etc., or a $C_{1-4}$alkylsulfonyl (e.g., methanesulfonyl, ethanesulfonyl, etc.) or a carbonyl or sulfonyl substituted aromatic or heterocyclic ring, e.g., benzenesulfonyl, benzoyl, pyridinesulfonyl, pyridinecarbonyl etc. The heterocycles are as described herein.

Examples of optionally substituted carbonyl groups, or sulfonyl groups include optionally substituted forms of such groups formed from various hydrocarbyls such as alkyl, alkenyl and 5- to 6-membered monocyclic aromatic group (e.g., phenyl, pyridyl, etc.), as described herein.

Therapeutic Indications

The invention provides methods of treating conditions that are modulated, directly or indirectly, by an O-GlcNAcase enzyme or by O-GlcNAc-modified protein levels, for example, a condition that is benefited by inhibition of an O-GlcNAcase enzyme or by an elevation of O-GlcNAc-modified protein levels. Such conditions include, without limitation, Glaucoma, Schizophrenia, tauopathies, such as Alzheimer's disease, neurodegenerative diseases, cardiovascular diseases, diseases associated with inflammation, diseases associated with immunosuppression and cancers. The compounds of the invention are also useful in the treatment of diseases or disorders related to deficiency or over-expression of O-GlcNAcase or accumulation or depletion of O-GlcNAc, or any disease or disorder responsive to glycosidase inhibition therapy. Such diseases and disorders include, but are not limited to, Glaucoma, Schizophrenia, neurodegenerative disorders, such as Alzheimer's disease (AD), or cancer. Such diseases and disorders may also include diseases or disorders related to the accumulation or deficiency in the enzyme OGT. Also included is a method of protecting or treating target cells expressing proteins that are modified by O-GlcNAc residues, the dysregulation of which modification results in disease or pathology. The term "treating" as used herein includes treatment, prevention, and amelioration.

In alternative embodiments, the invention provides methods of enhancing or elevating levels of protein O-GlcNAc modification in animal subjects, such as, veterinary and human subjects. This elevation of O-GlcNAc levels can be useful for the prevention or treatment of Alzheimer's disease; prevention or treatment of other neurodegenerative diseases (e.g. Parkinson's disease, Huntington's disease); providing neuroprotective effects; preventing damage to cardiac tissue; and treating diseases associated with inflammation or immunosuppression.

In alternative embodiments, the invention provides methods of selectively inhibiting an O-GlcNAcase enzyme in animal subjects, such as veterinary and human subjects.

In alternative embodiments, the invention provides methods of inhibiting phosphorylation of tau polypeptides, or inhibiting formation of NFTs, in animal subjects, such as, veterinary and human subjects. Accordingly, the compounds of the invention may be used to study and treat AD and other tauopathies.

In general, the methods of the invention are effected by administering a compound according to the invention to a subject in need thereof, or by contacting a cell or a sample with a compound according to the invention, for example, a pharmaceutical composition comprising a therapeutically effective amount of the compound according to Formula (I). More particularly, they are useful in the treatment of a disorder in which the regulation of O-GlcNAc protein modification is implicated, or any condition as described herein. Disease states of interest include Alzheimer's disease (AD) and related neurodegenerative tauopathies, in which abnormal hyperphosphorylation of the microtubule-associated protein tau is involved in disease pathogenesis. In some embodiments, the compounds may be used to block hyperphosphorylation of tau by maintaining elevated levels of O-GlcNAc on tau, thereby providing therapeutic benefit.

Tauopathies that may be treated with the compounds of the invention include: Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, and Tangle-only dementia.

The compounds of this invention are also useful in the treatment of conditions associate with tissue damage or stress, stimulating cells, or promoting differentiation of cells. Accordingly, in some embodiments, the compounds of this invention may be used to provide therapeutic benefit in a variety of conditions or medical procedures involving stress in cardiac tissue, including but not limited to: ischemia; hemorrhage; hypovolemic shock; myocardial infarction; an interventional cardiology procedure; cardiac bypass surgery; fibrinolytic therapy; angioplasty; and stent placement.

Compounds that selectively inhibit O-GlcNAcase activity may be used for the treatment of diseases that are associated with inflammation, including but not limited to, inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, systemic lupus erythematosus, myastenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition, compounds that affects levels of protein O-GlcNAc modification may be used for the treatment of diseases associated with immunosuppression, such as in individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; or immunosuppression due to congenital deficiency in receptor function or other causes.

The compounds of the invention may be useful for treatment of neurodegenerative diseases, including Parkinson's disease and Huntington's disease. Other conditions that may be treated are those triggered, affected, or in any other way correlated with levels of O-GlcNAc post-translational protein modification. It is expected that the compounds of this invention may be useful for the treatment of such conditions and in particular, but not limited to, the following for which a association with O-GlcNAc levels on proteins has been established: graft rejection, in particular but not limited to solid organ transplants, such as heart, lung, liver, kidney, and pancreas transplants (e.g. kidney and lung allografts); cancer, in particular but not limited to cancer of the breast, lung, prostate, pancreas, colon, rectum, bladder, kidney, ovary; as well as non-Hodgkin's lymphoma and melanoma; epilepsy, pain, or stroke, e.g., for neuroprotection following a stroke.

Pharmaceutical & Veterinary Compositions, Dosages, and Administration

Pharmaceutical compositions including compounds according to the invention, or for use according to the invention, are contemplated as being within the scope of the invention. In some embodiments, pharmaceutical compositions including an effective amount of a compound of Formula (I) are provided.

The compounds of formula (I) and their pharmaceutically acceptable salts, stereoisomers, solvates, and derivatives are useful because they have pharmacological activity in animals, including humans. In some embodiments, the compounds according to the invention are stable in plasma, when administered to a subject.

In some embodiments, compounds according to the invention, or for use according to the invention, may be provided in combination with any other active agents or pharmaceutical compositions where such combined therapy is useful to modulate O-GlcNAcase activity, for example, to treat neurodegenerative, inflammatory, cardiovascular, or immunoregulatory diseases, or any condition described herein. In some embodiments, compounds according to the invention, or for use according to the invention, may be provided in combination with one or more agents useful in the prevention or treatment of Alzheimer's disease. Examples of such agents include, without limitation,

- acetylcholine esterase inhibitors (AChEIs) such as Aricept® (Donepezil), Exelon® (Rivastigmine), Razadyne® (Razadyne ER®, Reminyl®, Nivalin®, Galantamine), Cognex® (Tacrine), Dimebon, Huperzine A, Phenserine, Debio-9902 SR (ZT-1 SR), Zanapezil (TAK0147), ganstigmine, NP7557, etc.;
- NMDA receptor antagonists such as Namenda® (Axura®, Akatinol®, Ebixa®, Memantine), Dimebon, SGS-742, Neramexane, Debio-9902 SR (ZT-1 SR), etc.;
- gamma-secretase inhibitors and/or modulators such as Flurizan™ (Tarenflurbil, MPC-7869, R-flurbiprofen), LY450139, MK 0752, E2101, BMS-289948, BMS-299897, BMS-433796, LY-411575, GSI-136, etc.;
- beta-secretase inhibitors such as ATG-Z1, CTS-21166, etc.;
- alpha-secretase activators, such as NGX267, etc;
- amyloid-β aggregation and/or fibrillization inhibitors such as Alzhemed™ (3APS, Tramiprosate, 3-amino-1-propanesulfonic acid), AL-108, AL-208, AZD-103, PBT2, Cereact, ONO-2506PO, PPI-558, etc.;
- tau aggregation inhibitors such as methylene blue, etc.;
- microtubule stabilizers such as AL-108, AL-208, paclitaxel, etc.;
- RAGE inhibitors, such as TTP488, etc.;
- 5-HT1a receptor antagonists, such as Xaliproden, Lecozotan, etc.;
- 5-HT4 receptor antagonists, such as PRX-03410, etc.;
- kinase inhibitors such as SRN-003-556, amfurindamide, LiCl, AZD1080, NP031112, SAR-502250, etc.
- humanized monoclonal anti-β antibodies such as Bapineuzumab (AAB-001), LY2062430, RN1219, ACU-5A5, etc.;
- amyloid vaccines such as AN-1792, ACC-001
- neuroprotective agents such as Cerebrolysin, AL-108, AL-208, Huperzine A, etc.;
- L-type calcium channel antagonists such as MEM-1003, etc.;
- nicotinic receptor antagonists, such as AZD3480, GTS-21, etc.;
- nicotinic receptor agonists, such as MEM 3454, Nefiracetam, etc.;
- peroxisome proliferator-activated receptor (PPAR) gamma agonists such as Avandia® (Rosglitazone), etc.;
- phosphodiesterase IV (PDE4) inhibitors, such as MK-0952, etc.;
- hormone replacement therapy such as estrogen (Premarin), etc.;
- monoamine oxidase (MAO) inhibitors such as NS2330, Rasagiline (Azilect®), TVP-1012, etc.;
- AMPA receptor modulators such as Ampalex (CX 516), etc.;
- nerve growth factors or NGF potentiators, such as CERE-110 (AAV-NGF), T-588, T-817MA, etc.;
- agents that prevent the release of luteinizing hormone (LH) by the pituitary gland, such as leuoprolide (VP-4896), etc.;
- GABA receptor modulators such as AC-3933, NGD 97-1, CP-457920, etc.;
- benzodiazepine receptor inverse agonists such as SB-737552 (S-8510), AC-3933, etc.;
- noradrenaline-releasing agents such as T-588, T-817MA, etc.

It is to be understood that combination of compounds according to the invention, or for use according to the invention, with Alzheimer's agents is not limited to the examples described herein, but includes combination with any agent useful for the treatment of Alzheimer's disease. Combination of compounds according to the invention, or for use according to the invention, and other Alzheimer's agents may be administered separately or in conjunction. The administration of one agent may be prior to, concurrent to, or subsequent to the administration of other agent(s).

In alternative embodiments, the compounds may be supplied as "prodrugs" or protected forms, which release the compound after administration to a subject. For example, the compound may carry a protective group which is split off by hydrolysis in body fluids, e.g., in the bloodstream, thus releasing the active compound or is oxidized or reduced in body fluids to release the compound. Accordingly, a "prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a subject.

The term "prodrug" is also meant to include any covalently bonded carriers which release the active compound of the invention in vivo when such prodrug is administered to a subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and acetamide, formamide, and benzamide derivatives of amine functional groups in the compounds of the invention and the like.

Additional examples of prodrugs for the compounds of the invention include acetonide derivatives (also known as isopropylidine derivatives) in which two $OR^1$ groups in Formula (I) may be linked in a ring, for example, as in Formulae (II) and (III) shown below. Such acetonide groups may be cleaved in vivo to liberate the parent compound of the invention, making these acetonide derivatives prodrugs.

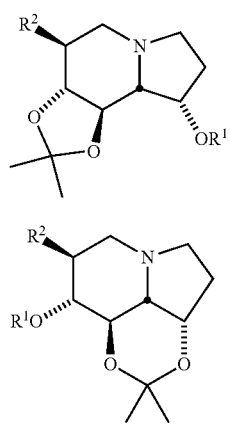

A discussion of prodrugs may be found in "Smith and Williams' Introduction to the Principles of Drug Design," H. J. Smith, Wright, Second Edition, London (1988); Bundgard, H., *Design of Prodrugs* (1985), pp. 7-9, 21-24 (Elsevier, Amsterdam); The Practice of Medicinal Chemistry, Camille G. Wermuth et al., Ch 31, (Academic Press, 1996); A Textbook of Drug Design and Development, P. Krogsgaard-Larson and H. Bundgaard, eds. Ch 5, pgs 113 191 (Harwood Academic Publishers, 1991); Higuchi, T., et al., "Pro-drugs as Novel Delivery Systems," A.C.S. Symposium Series, Vol. 14; or in Bioreversible Carriers in Drug Design, ed. Edward B. Roche, American Pharmaceutical Association and Pergamon Press, 1987, all of which are incorporated in full by reference herein.

Suitable prodrug forms of the compounds of the invention include embodiments in which $R^1$ is C(O)R, where R is optionally substituted alkyl, alkenyl, alkynyl, aryl, or heteroaryl. In these cases the ester groups may be hydrolyzed in vivo (e.g. in bodily fluids), releasing the active compounds in which $R^1$ is H. Preferred prodrug embodiments of the invention are the compounds of Formula (I) where $R^1$ is $C(O)CH_3$.

Compounds according to the invention, or for use according to the invention, can be provided alone or in combination with other compounds in the presence of a liposome, an adjuvant, or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. Compounds according to the invention may be provided chronically or intermittently. "Chronic" administration refers to administration of the compound(s) in a continuous mode as opposed to an acute mode, so as to maintain the initial therapeutic effect (activity) for an extended period of time. "Intermittent" administration is treatment that is not consecutively done without interruption, but rather is cyclic in nature. The terms "administration," "administrable," or "administering" as used herein should be understood to mean providing a compound of the invention to the subject in need of treatment.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved, for example, by the United States Food and Drug Administration or other governmental agency as being acceptable for use in humans or domestic animals.

The compounds of the present invention may be administered in the form of pharmaceutically acceptable salts. In such cases, pharmaceutical compositions in accordance with this invention may comprise a salt of such a compound, preferably a physiologically acceptable salt, which are known in the art. In some embodiments, the term "pharmaceutically acceptable salt" as used herein means an active ingredient comprising compounds of Formula 1 used in the form of a salt thereof, particularly where the salt form confers on the active ingredient improved pharmacokinetic properties as compared to the free form of the active ingredient or other previously disclosed salt form.

A "pharmaceutically acceptable salt" includes both acid and base addition salts. A "pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

A "pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrab amine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Thus, the term "pharmaceutically acceptable salt" encompasses all acceptable salts including but not limited to acetate, lactobionate, benzenesulfonate, laurate, benzoate, malate, bicarbonate, maleate, bisulfate, mandelate, bitartarate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of the compounds of the present invention can be used as a dosage for modifying solubility or hydrolysis characteristics, or can be used in sustained release or prodrug formulations. Also, pharmaceutically acceptable salts of the compounds of this invention may include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

Pharmaceutical formulations will typically include one or more carriers acceptable for the mode of administration of the preparation, be it by injection, inhalation, topical administration, lavage, or other modes suitable for the selected treatment. Suitable carriers are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in Remington: the *Science & Practice of Pharmacy* by Alfonso Gennaro, 20$^{th}$ ed., Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds.

Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The compounds or pharmaceutical compositions according to the present invention may be administered by oral or non-oral, e.g., intramuscular, intraperitoneal, intravenous, intracisternal injection or infusion, subcutaneous injection, transdermal or transmucosal routes. In some embodiments, compounds or pharmaceutical compositions in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the compound over a period of time. The compounds may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaryies. In some embodiments, compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The compounds of the invention may be used to treat animals, including mice, rats, horses, cattle, sheep, dogs, cats, and monkeys. However, compounds of the invention can also be used in other organisms, such as avian species (e.g., chickens). The compounds of the invention may also be effective for use in humans. The term "subject" or alternatively referred to herein as "patient" is intended to be referred to an animal, preferably a mammal, most preferably a human, who has been the object of treatment, observation or experiment. However, the compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition requiring modulation of O-GlcNAcase activity.

An "effective amount" of a compound according to the invention includes a therapeutically effective amount or a prophylactically effective amount. A "therapeutically effective amount" refers to an amount effective, at dosages and for periods of time necessary, to achieve the desired therapeutic result, such as inhibition of an O-GlcNAcase, elevation of O-GlcNAc levels, inhibition of tau phosphorylation, or any condition described herein. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as inhibition of an O-GlcNAcase, elevation of O-GlcNAc levels, inhibition of tau phosphorylation, or any condition described herein. Typically, a prophylactic dose is used in subjects prior to or at an earlier stage of disease, so that a prophylactically effective amount may be less than a therapeutically effective amount. A suitable range for therapeutically or prophylactically effective amounts of a compound may be any integer from 0.1 nM-0.1M, 0.1 nM-0.05M, 0.05 nM-15 µM or 0.01 nM-10 µM.

In alternative embodiments, in the treatment or prevention of conditions which require modulation of O-GlcNAcase activity, an appropriate dosage level will generally be about 0.01 to 500 mg per kg subject body weight per day, and can be administered in singe or multiple doses. In some embodiments, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. In general, compounds of the invention should be used without causing substantial toxicity, and as described herein, the compounds exhibit a suitable safety profile for therapeutic use. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

Other Uses and Assays

A compound of Formula (I) may be used in screening assays for compounds which modulate the activity of glycosidase enzymes, preferably the O-GlcNAcase enzyme. The ability of a test compound to inhibit O-GlcNAcase-dependent cleavage of O-GlcNAc from a model substrate may be measured using any assays, as described herein or known to one of ordinary skill in the art. For example, a fluoresence or UV-based assay known in the art may be used. A "test compound" is any naturally-occurring or artificially-derived chemical compound. Test compounds may include, without limitation, peptides, polypeptides, synthesised organic molecules, naturally occurring organic molecules, and nucleic acid molecules. A test compound can "compete" with a known compound such as a compound of Formula (I) by, for example, interfering with inhibition of O-GlcNAcase-dependent cleavage of O-GlcNAc or by interfering with any biological response induced by a compound of Formula (I).

Generally, a test compound can exhibit any value between 10% and 200%, or over 500%, modulation when compared to a compound of Formula (I) or other reference compound. For example, a test compound may exhibit at least any positive or negative integer from 10% to 200% modulation, or at least any positive or negative integer from 30% to 150% modulation, or at least any positive or negative integer from 60% to 100% modulation, or any positive or negative integer over 100% modulation. A compound that is a negative modulator will in general decrease modulation relative to a known compound, while a compound that is a positive modulator will in general increase modulation relative to a known compound.

In general, test compounds are identified from large libraries of both natural products or synthetic (or semi-synthetic) extracts or chemical libraries according to methods known in the art. Those skilled in the field of drug discovery and development will understand that the precise source of test extracts or compounds is not critical to the method(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available. Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla., USA), and PharmaMar, Mass., USA. In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

When a crude extract is found to modulate inhibition of O-GlcNAcase-dependent cleavage of O-GlcNAc, or any biological response induced by a compound of Formula (I), further fractionation of the positive lead extract is necessary to isolate chemical constituents responsible for the observed effect. Thus, the goal of the extraction, fractionation, and purification process is the careful characterization and identification of a chemical entity within the crude extract having O-GlcNAcase-inhibitory activities. The same assays described herein for the detection of activities in mixtures of compounds can be used to purify the active component and to test derivatives thereof. Methods of fractionation and purification of such heterogeneous extracts are known in the art. If desired, compounds shown to be useful agents for treatment are chemically modified according to methods known in the art. Compounds identified as being of therapeutic, prophylactic, diagnostic, or other value may be subsequently analyzed using a suitable animal model, as described herein on known in the art.

In some embodiments, the compounds described herein (e.g., the compounds of Formula I) or test compounds may be analyzed using established cellular[118-120] and/or transgenic animal models of disease[32,33] and the ability of the compounds to, for example, block the formation of toxic tau species determined. Such analyses may be used for example to determine or confirm the efficacy of the compounds in treating or preventing pathology associated with the accumulation of toxic tau species (for example, Alzheimer's disease and other tauopathies).

In some embodiments, the compounds described herein (e.g., the compounds of Formula I) or test compounds may be analyzed using established cellular stress assays[105,116,117] and/or animal models of ischemia-reperfusion[70,114] or trauma-hemorrhage.[72,112,115] Such analyses may be used for example to determine or confirm the efficacy of the compounds in treating or preventing pathology associated with cellular stress (including ischemia, hemorrhage, hypovolemic shock, myocardial infarction, and other cardiovascular disorders) or in treating or preventing tissue damage or promoting functional recovery.

In some embodiments, the compounds are useful in the development of animal models for studying diseases or disorders related to deficiencies in O-GlcNAcase, over-expression of O-GlcNAcase, accumulation of O-GlcNAc, depletion of O-GlcNAc, and for studying treatment of diseases and disorders related to deficiency or over-expression of O-GlcNAcase, or accumulation or depletion of O-GlcNAc. Such diseases and disorders include neurodegenerative diseases, including Alzheimer's disease, and cancer.

Various alternative embodiments and examples of the invention are described herein. These embodiments and examples are illustrative and should not be construed as limiting the scope of the invention.

tosyl group with sodium in napthalene gives C in 91% yield, which is then converted in quantitative yield to the amino oxazoline D by reaction with freshly-distilled methyl triflate followed by dimethyl amine. Dihydroxylation of the double bond in D using trifluroperacetic acid in TFA then warming with aqueous TFA, followed by benzyl deprotection with hydrogenolysis provides allosamizoline 2 in 67% yield. Numerous alternative synthetic routes are available for the preparation of 2, as described in the references cited herein.[121-131]

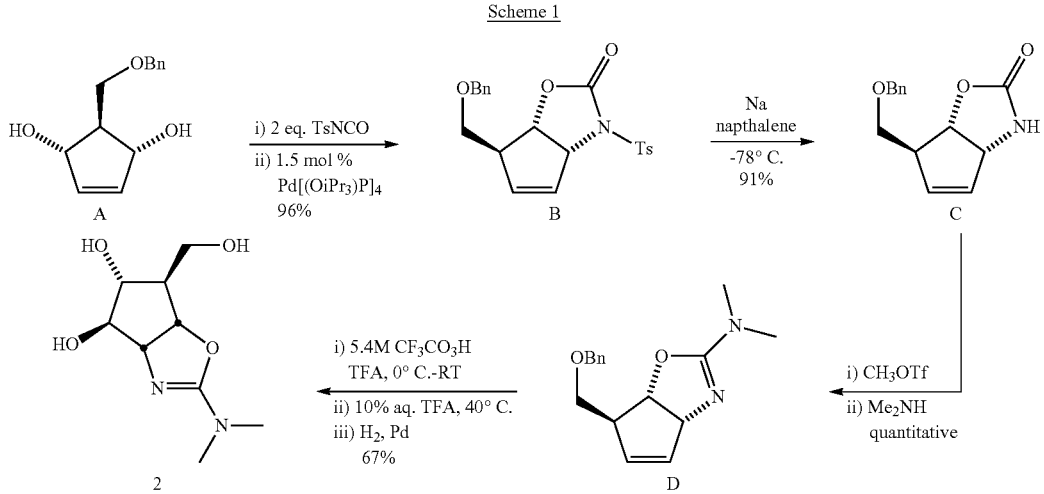

Scheme 1

EXAMPLES

The following examples are intended to illustrate embodiments of the invention and are not intended to be construed in a limiting manner.

Example 1

Compounds 1 and 2 (allosamizoline) are prepared via known synthetic methods.[121-131] For example, following the synthetic route of Trost et al.[126] (Scheme 1), reaction of the diol A with 2 equiv. TsNCO followed by catalytic palladium provides the cyclic carbamate B in 96% yield. Removal of the

Example 2

Compounds of the invention having general structure F are prepared according to the sequence described in Scheme 2. Thus, starting from the intermediate C,[126] treatment with methyl triflate followed by the requisite primary or secondary amine (analagous to the procedure described by Trost et al.[126]) provides the amino oxazolines E. Dihydroxylation of these materials followed by deprotection using the same conditions described in Scheme 1 provides the desired products F.

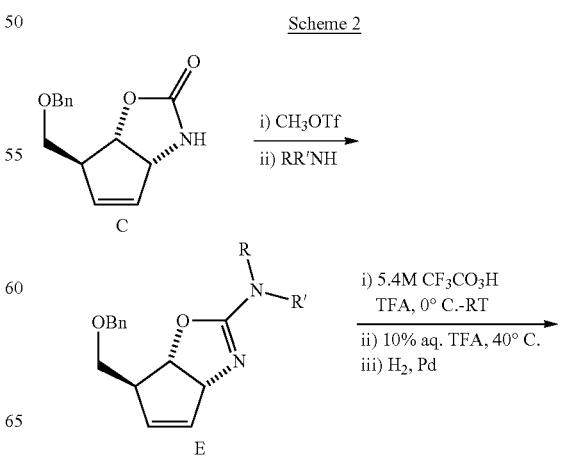

Scheme 2

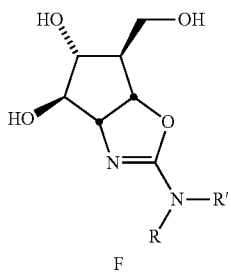

Example 3

Compounds of the invention having general structure K are prepared according to the sequence described in Scheme 3. Thus, starting from the intermediate G,[132] treatment with the appropriate isothiocyanate provides the ureas H. Mesylation of the alcohol function in H provides intermediates I. Treatment of these compounds with potassium iodide in acetone converts the mesylate to an iodo function with inversion of stereochemistry; under the reaction conditions, the thiourea cyclizes onto the iodo group to give intermediates J. Deprotection of the TBDMS group in these materials with TBAF, followed by benzyl deprotection using hydrogenolysis furnishes the desired products K.

Example 5

Compound 2 (allosamizoline): (3aR,4R,5R,6R,6aS)-2-(dimethylamino)-6-(hydroxymethyl)-4,5,6,6a-tetrahydro-3aH-cyclopenta[d]oxazole-4,5-diol

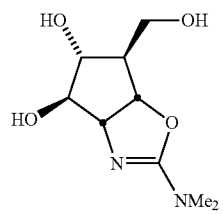

Compound 2 was purchased as the hydrochloride salt from a commercial supplier. $^1$H NMR (200 MHz, D$_2$O) δ 2.25-2.40 (m, 1H), 3.00 (s, 3H), 3.02 (s, 3H), 3.59-3.87 (m, 3H), 4.02 (dd, 1H, J=7, 5 Hz), 4.27 (dd, 1H, J=9, 6 Hz), 5.26 (dd, 1H, J=9, 5 Hz); $^{13}$C NMR (50 MHz, D$_2$O) δ 37.3, 37.5, 51.3, 59.3, 63.6, 74.8, 81.6, 86.7, 160.6; MS (EI, free base): m/z 217 (M+1).

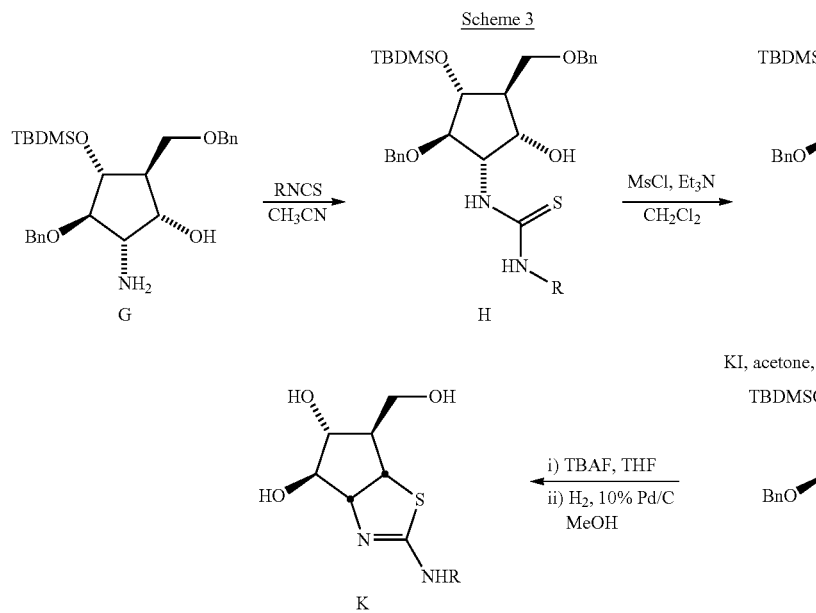

Scheme 3

Example 4

Compounds of the invention having general structure L are prepared according to the sequence described in Scheme 4. Treatment of compounds K with the appropriate secondary amine in water with heating provided the desired products L (e.g., see Kinoshita et al.[133])

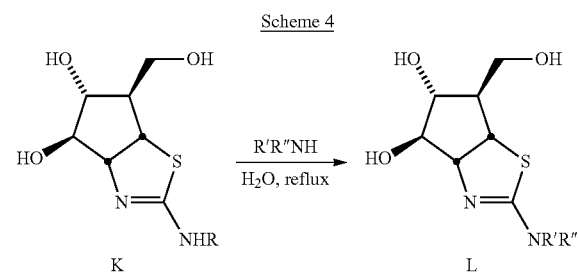

Scheme 4

Example 6

Assay for Determination of K$_1$ Values for Inhibition of O-GlcNAcase Activity

Experimental Procedure for Kinetic Analyses:

Enzymatic reactions are carried out in PBS buffer (pH 7.4) using pNP-GlcNAc as a substrate (0.5 mM) and monitored continuously at 37° C. at 400 nm using a Cary 3E UV-VIS spectrophotometer equipped with a Peltier temperature controller. Reactions are pre-heated in a 500 µL quartz cuvette for approximately 5 minutes followed by addition of 10 µL enzyme via syringe (final enzyme concentration 0.002 mg/mL). Reaction velocities are determined by linear regression of the linear region of the reaction progress curve between the first and third minutes. An inhibitor concentration range of ⅕ to 5 times K$_1$ is used in each case. When tested in this assay, many of the compounds described herein exhibit $K_1$ values for inhibition of O-GlcNAcase in the range 1 nM-50 μM. All $K_1$ values are determined using linear regression of Dixon plots.

Example 7

Assay for Determination of $K_1$ Values for Inhibition of β-Hexosaminidase Activity Experimental Procedure for Kinetic Analyses:

All enzymatic assays are carried out in triplicate at 37° C. using a stopped assay procedure by measuring the amount of 4-nitrophenolate liberated as determined by absorption measurements at 400 nm. Reactions (50 μL) are initiated by the addition, via syringe, of enzyme (3 μL). Time-dependent assay of β-hexosaminidase has revealed that the enzyme is stable in the buffer over the period of the assay: 50 mM citrate, 100 mM NaCl, 0.1% BSA, pH 4.25. β-hexosaminidase is used at a concentration of 0.036 mg/mL with pNP-GlcNAc as a substrate at a concentration of 0.5 mM. The inhibitor is tested at five concentrations ranging from 5 times to ⅕ $K_1$. $K_1$ values are determined by linear regression of data from Dixon plots.

When tested in this assay, many of the compounds described herein exhibit $K_1$ values for inhibition of β-hexosaminidase in the range 1 μM-10 mM. For example, the $K_1$ value for inhibition of O-GlcNAcase shown in Table 3 was obtained for compound 2. This $K_1$ value was determined using linear regression of a Dixon plot.

TABLE 3

Inhibition constant for O-GlcNAcase.

| Compound | O-GlcNAcase $K_I$ (μM) |
|---|---|
| 2 | 40 |

The selectivity ratio for inhibition of O-GlcNAcase over β-hexosaminidase is defined here as:

$K_{1(\beta\text{-}hexosaminidase)}/K_{1(O\text{-}GlcNAcase)}$

In general, the compounds described herein should exhibit a selectivity ratio in the range of about 10 to 100000. Thus, many compounds of the invention exhibit high selectivity for inhibition of O-GlcNAcase over β-hexosaminidase.

The present invention has been described with regard to one or more embodiments. However, it will be apparent to persons skilled in the art that a number of variations and modifications can be made without departing from the scope of the invention as defined in the claims.

REFERENCES

1. C. R. Torres, G. W. Hart, *J Biol Chem* 1984, 259, 3308.
2. R. S. Haltiwanger, G. D. Holt, G. W. Hart, *J Biol Chem* 1990, 265, 2563.
3. L. K. Kreppel, M. A. Blomberg, G. W. Hart, *J Biol Chem* 1997, 272, 9308.
4. W. A. Lubas, D. W. Frank, M. Krause, J. A. Hanover, *J Biol Chem* 1997, 272, 9316.
5. W. A. Lubas, J. A. Hanover, *J Biol Chem* 2000, 275, 10983.
6. D. L. Dong, G. W. Hart, *J Biol Chem* 1994, 269, 19321.
7. Y. Gao, L. Wells, F. I. Comer, G. J. Parker, G. W. Hart, *J Biol Chem* 2001, 276, 9838.
8. E. P. Roquemore, M. R. Chevrier, R. J. Cotter, G. W. Hart, *Biochemistry* 1996, 35, 3578.
9. S. P. Jackson, R. Tjian, *Cell* 1988, 55, 125.
10. W. G. Kelly, M. E. Dahmus, G. W. Hart, *J Biol Chem* 1993, 268, 10416.
11. M. D. Roos, K. Su, J. R. Baker, J. E. Kudlow, *Mol Cell Biol* 1997, 17, 6472.
12. N. Lamarre-Vincent, L. C. Hsieh-Wilson, *J Am Chem Soc* 2003, 125, 6612.
13. F. Zhang, K. Su, X. Yang, D. B. Bowe, A. J. Paterson, J. E. Kudlow, *Cell* 2003, 115, 715.
14. K. Vosseller, L. Wells, M. D. Lane, G. W. Hart, *Proc Natl Acad Sci USA* 2002, 99, 5313.
15. W. A. Lubas, M. Smith, C. M. Starr, J. A. Hanover, *Biochemistry* 1995, 34, 1686.
16. L. S. Griffith, B. Schmitz, *Biochem Biophys Res Commun* 1995, 213, 424.
17. R. N. Cole, G. W. Hart, *J Neurochem* 1999, 73, 418.
18. I. Braidman, M. Carroll, N. Dance, D. Robinson, *Biochem J* 1974, 143, 295.
19. R. Ueno, C. S. Yuan, *Biochim Biophys Acta* 1991, 1074, 79.
20. C. Toleman, A. J. Paterson, T. R. Whisenhunt, J. E. Kudlow, *J Biol Chem* 2004.
21. F. Liu, K. Iqbal, I. Grundke-Iqbal, G. W. Hart, C. X. Gong, *Proc Natl Acad Sci USA* 2004, 101, 10804.
22. T. Y. Chou, G. W. Hart, *Adv Exp Med Biol* 2001, 491, 413.
23. M. Goedert, M. G. Spillantini, N. J. Cairns, R. A. Crowther, *Neuron* 1992, 8, 159.
24. M. Goedert, M. G. Spillantini, R. Jakes, D. Rutherford, R. A. Crowther, *Neuron* 1989, 3, 519.
25. E. Kopke, Y. C. Tung, S. Shaikh, A. C. Alonso, K. Iqbal, I. Grundke-Iqbal, *J Biol Chem* 1993, 268, 24374.
26. H. Ksiezak-Reding, W. K. Liu, S. H. Yen, *Brain Res* 1992, 597, 209.
27. B. Henrissat, A. Bairoch, *Biochem J* 1996, 316 (Pt 2), 695.
28. B. Henrissat, A. Bairoch, *Biochem J* 1993, 293 (Pt 3), 781.
29. C. X. Gong, F. Liu, I. Grundke-Iqbal, K. Iqbal, *J Neural Transm* 2005, 112, 813.
30. K. Iqbal, C. Alonso Adel, E. El-Akkad, C. X. Gong, N. Hague, S. Khatoon, I. Tsujio, I. Grundke-Iqbal, *J Neural Transm Suppl* 2002, 309.
31. K. Iqbal, C. Alonso Adel, E. El-Akkad, C. X. Gong, N. Hague, S. Khatoon, J. J. Pei, H. Tanimukai, I. Tsujio, et al., *J Mol Neurosci* 2003, 20, 425.
32. W. Noble, E. Planel, C. Zehr, V. Olm, J. Meyerson, F. Suleman, K. Gaynor, L. Wang, J. LaFrancois, et al., *Proc Natl Acad Sci USA* 2005, 102, 6990.
33. S. Le Cone, H. W. Klafki, N. Plesnila, G. Hubinger, A. Obermeier, H. Sahagun, B. Monse, P. Seneci, J. Lewis, et al., *Proc Natl Acad Sci USA* 2006, 103, 9673.
34. S. J. Liu, J. Y. Zhang, H. L. Li, Z. Y. Fang, Q. Wang, H. M. Deng, C. X. Gong, I. Grundke-Iqbal, K. Iqbal, et al., *J Biol Chem* 2004, 279, 50078.
35. G. Li, H. Yin, J. Kuret, *J Biol Chem* 2004, 279, 15938.
36. T. Y. Chou, G. W. Hart, C. V. Dang, *J Biol Chem* 1995, 270, 18961.
37. X. Cheng, G. W. Hart, *J Biol Chem* 2001, 276, 10570.
38. X. Cheng, R. N. Cole, J. Zaia, G. W. Hart, *Biochemistry* 2000, 39, 11609.
39. L. S. Griffith, B. Schmitz, *Eur J Biochem* 1999, 262, 824.
40. K. Kamemura, G. W. Hart, *Prog Nucleic Acid Res Mol Biol* 2003, 73, 107.
41. L. Wells, L. K. Kreppel, F. I. Comer, B. E. Wadzinski, G. W. Hart, *J Biol Chem* 2004, 279, 38466.
42. L. Bertram, D. Blacker, K. Mullin, D. Keeney, J. Jones, S. Basu, S. Yhu, M. G. McInnis, R. C. Go, et al., *Science* 2000, 290, 2302.

43. S. Hoyer, D. Blum-Degen, H. G. Bernstein, S. Engelsberger, J. Humrich, S. Laufer, D. Muschner, A. Thalheimer, A. Turk, et al., *Journal of Neural Transmission* 1998, 105, 423.
44. C. X. Gong, F. Liu, I. Grundke-Iqbal, K. Iqbal, *Journal of Alzheimers Disease* 2006, 9, 1.
45. W. J. Jagust, J. P. Seab, R. H. Huesman, P. E. Valk, C. A. Mathis, B. R. Reed, P. G. Coxson, T. F. Budinger, *Journal of Cerebral Blood Flow and Metabolism* 1991, 11, 323.
46. S. Hoyer, *Experimental Gerontology* 2000, 35, 1363.
47. S. Hoyer, in *Frontiers in Clinical Neuroscience: Neurodegeneration and Neuroprotection*, Vol. 541, 2004, pp. 135.
48. R. N. Kalaria, S. I. Harik, *Journal of Neurochemistry* 1989, 53, 1083.
49. I. A. Simpson, K. R. Chundu, T. Davieshill, W. G. Honer, P. Davies, *Annals of Neurology* 1994, 35, 546.
50. S. M. de la Monte, J. R. Wands, *Journal of Alzheimers Disease* 2005, 7, 45.
51. X. W. Zhu, G. Perry, M. A. Smith, *Journal of Alzheimers Disease* 2005, 7, 81.
52. J. C. de la Tone, *Neurological Research* 2004, 26, 517.
53. S. Marshall, W. T. Garvey, R. R. Traxinger, *Faseb* 11991, 5, 3031.
54. S. P. Iyer, Y. Akimoto, G. W. Hart, *J Biol Chem* 2003, 278, 5399.
55. K. Brickley, M. J. Smith, M. Beck, F. A. Stephenson, *J Biol Chem* 2005, 280, 14723.
56. S. Knapp, C. H. Yang, T. Haimowitz, *Tetrahedron Letters* 2002, 43, 7101.
57. S. P. Iyer, G. W. Hart, *J Biol Chem* 2003, 278, 24608.
58. M. Jinek, J. Rehwinkel, B. D. Lazarus, E. Izaurralde, J. A. Hanover, E. Conti, *Nat Struct Mol Biol* 2004, 11, 1001.
59. K. Kamemura, B. K. Hayes, F. I. Comer, G. W. Hart, *J Biol Chem* 2002, 277, 19229.
60. Y. Deng, B. Li, F. Liu, K. Iqbal, I. Grundke-Iqbal, R. Brandt, C.-X. Gong, *FASEB J.* 2007, fj.07.
61. L. F. Lau, J. B. Schachter, P. A. Seymour, M. A. Sanner, *Curr Top Med Chem* 2002, 2, 395.
62. M. P. Mazanetz, P. M. Fischer, *Nature Reviews Drug Discovery* 2007, 6, 464.
63. S. A. Yuzwa, M. S. Macauley, J. E. Heinonen, X. Shan, R. J. Dennis, Y. He, G. E. Whitworth, K. A. Stubbs, E. J. McEachern, et al., *Nat Chem Biol* 2008, 4, 483.
64. P. Bounelis, J. Liu, Y. Pang, J. C. Chatham, R. B. Marchase, *Shock* 2004, 21 170 *Suppl.* 2, 58.
65. N. Fulop, V. Champattanachal, R. B. Marchase, J. C. Chatham, *Circulation Research* 2005, 97, E28.
66. J. Liu, R. B. Marchase, J. C. Chatham, *Faseb Journal* 2006, 20, A317.
67. R. Marchase, P. Bounelis, J. Chatham, I. Chaudry, Y. Pang, PCT Int. Appl. WO 2006016904 2006.
68. N. Fulop, P. P. Wang, R. B. Marchase, J. C. Chatham, *Journal of Molecular and Cellular Cardiology* 2004, 37, 286.
69. N. Fulop, P. P. Wang, R. B. Marchase, J. C. Chatham, *Faseb Journal* 2005, 19, A689.
70. J. Liu, R. B. Marchase, J. C. Chatham, *Journal of Molecular and Cellular Cardiology* 2007, 42, 177.
71. L. G. Not, C. A. Brocks, N. Fulop, R. B. Marchase, J. C. Chatham, *Faseb Journal* 2006, 20, A1471.
72. S. L. Yang, L. Y. Zou, P. Bounelis, I. Chaudry, J. C. Chatham, R. B. Marchase, *Shock* 2006, 25, 600.
73. L. Y. Zou, S. L. Yang, P. Bounelis, I. H. Chaudry, J. C. Chatham, R. B. Marchase, *Faseb Journal* 2005, 19, A 1224.
74. R. B. Marchase, J. Liu, L. Y. Zou, V. Champattanachai, Y. Pang, N. Fulop, P. P. Wang, S. L. Yang, P. Bounelis, et al., *Circulation* 2004, 110, 1099.
75. J. Liu, Y. Pang, T. Chang, P. Bounelis, J. C. Chatham, R. B. Marchase, *Journal of Molecular and Cellular Cardiology* 2006, 40, 303.
76. J. Liu, J. C. Chatham, R. B. Marchase, *Faseb Journal* 2005, 19, A691.
77. T. Nagy, V. Champattanachai, R. B. Marchase, J. C. Chatham, *American Journal of Physiology-Cell Physiology* 2006, 290, C57.
78. N. Fulop, R. B. Marchase, J. C. Chatham, *Cardiovascular Research* 2007, 73, 288.
79. T. Lefebvre, C. Guinez, V. Dehennaut, O. Beseme-Dekeyser, W. Morelle, J. C. Michalski, *Expert Review of Proteomics* 2005, 2, 265.
80. L. Wells, K. Vosseller, G. W. Hart, *Science* 2001, 291, 2376.
81. J. A. Hanover, *FASEB J* 2001, 15, 1865.
82. D. A. McClain, W. A. Lubas, R. C. Cooksey, M. Hazel, G. J. Parker, D. C. Love, J. A. Hanover, *Proc Natl Acad Sci USA* 2002, 99, 10695.
83. P. J. Yao, P. D. Coleman, *J Neurosci* 1998, 18, 2399.
84. W. H. Yang, J. E. Kim, H. W. Nam, J. W. Ju, H. S. Kim, Y. S. Kim, J. W. Cho, *Nature Cell Biology* 2006, 8, 1074.
85. B. Triggs-Raine, D. J. Mahuran, R. A. Gravel, *Adv Genet* 2001, 44, 199.
86. D. Zhou, J. Mattner, C. Cantu Iii, N. Schrantz, N. Yin, Y. Gao, Y. Sagiv, K. Hudspeth, Y. Wu, et al., *Science* 2004.
87. G. Legler, E. Lullau, E. Kappes, F. Kastenholz, *Biochim Biophys Acta* 1991, 1080, 89.
88. M. Horsch, L. Hoesch, A. Vasella, D. M. Rast, *Eur J Biochem* 1991, 197, 815.
89. J. Liu, A. R. Shikhman, M. K. Lotz, C. H. Wong, *Chem Biol* 2001, 8, 701.
90. S. Knapp, D. J. Vocadlo, Z. N. Gao, B. Kirk, J. P. Lou, S. G. Withers, *J. Am. Chem. Soc.* 1996, 118, 6804.
91. V. H. Lillelund, H. H. Jensen, X. Liang, M. Bols, *Chem Rev* 2002, 102, 515.
92. R. J. Konrad, I. Mikolaenko, J. F. Tolar, K. Liu, J. E. Kudlow, *Biochem J* 2001, 356, 31.
93. K. Liu, A. J. Paterson, F. Zhang, J. McAndrew, K. Fukuchi, J. M. Wyss, L. Peng, Y. Hu, J. E. Kudlow, *J Neurochem* 2004, 89, 1044.
94. G. Parker, R. Taylor, D. Jones, D. McClain, *J Biol Chem* 2004, 279, 20636.
95. E. B. Arias, J. Kim, G. D. Cartee, *Diabetes* 2004, 53, 921.
96. A. Junod, A. E. Lambert, L. Orci, R. Pictet, A. E. Gonet, A. E. Renold, *Proc Soc Exp Biol Med* 1967, 126, 201.
97. R. A. Bennett, A. E. Pegg, *Cancer Res* 1981, 41, 2786.
98. K. D. Kroncke, K. Fehsel, A. Sommer, M. L. Rodriguez, V. Kolb-Bachofen, *Biol Chem Hoppe Seyler* 1995, 376, 179.
99. H. Yamamoto, Y. Uchigata, H. Okamoto, *Nature* 1981, 294, 284.
100. K. Yamada, K. Nonaka, T. Hanafusa, A. Miyazaki, H. Toyoshima, S. Tarui, *Diabetes* 1982, 31, 749.
101. V. Burkart, Z. Q. Wang, J. Radons, B. Heller, Z. Herceg, L. Stingl, E. F. Wagner, H. Kolb, *Nat Med* 1999, 5, 314.
102. M. D. Roos, W. Xie, K. Su, J. A. Clark, X. Yang, E. Chin, A. J. Paterson, J. E. Kudlow, *Proc Assoc Am Physicians* 1998, 110, 422.
103. Y. Gao, G. J. Parker, G. W. Hart, *Arch Biochem Biophys* 2000, 383, 296.
104. R. Okuyama, M. Yachi, *Biochem Biophys Res Commun* 2001, 287, 366.

105. N. E. Zachara, N. O'Donnell, W. D. Cheung, J. J. Mercer, J. D. Marth, G. W. Hart, *J Biol Chem* 2004, 279, 30133.
106. J. A. Hanover, Z. Lai, G. Lee, W. A. Lubas, S. M. Sato, *Arch Biochem Biophys* 1999, 362, 38.
107. K. Liu, A. J. Paterson, R. J. Konrad, A. F. Parlow, S. Jimi, M. Roh, E. Chin, Jr., J. E. Kudlow, *Mol Cell Endocrinol* 2002, 194, 135.
108. M. S. Macauley, G. E. Whitworth, A. W. Debowski, D. Chin, D. J. Vocadlo, *J Biol Chem* 2005, 280, 25313.
109. B. L. Mark, D. J. Vocadlo, S. Knapp, B. L. Triggs-Raine, S. G. Withers, M. N. James, *J Biol Chem* 2001, 276, 10330.
110. R. S. Haltiwanger, K. Grove, G. A. Philipsberg, *J Biol Chem* 1998, 273, 3611.
111. D. J. Miller, X. Gong, B. D. Shur, *Development* 1993, 118, 1279.
112. L. Y. Zou, S. L. Yang, S. H. Hu, I. H. Chaudry, R. B. Marchase, J. C. Chatham, *Shock* 2007, 27, 402.
113. J. B. Huang, A. J. Clark, H. R. Petty, *Cellular Immunology* 2007, 245, 1.
114. U. J. G. Conference, in US/Japan Glyco 2004 Conference, Honolulu, Hi., 2004.
115. L. Y. Zou, S. L. Yang, S. H. Hu, I. H. Chaudry, R. B. Marchase, J. C. Chatham, *Faseb Journal* 2006, 20, A1471.
116. V. Champattanachai, R. B. Marchase, J. C. Chatham, *American Journal of Physiology-Cell Physiology* 2007, 292, C178.
117. V. Champattanachai, R. B. Marchase, J. C. Chatham, *American Journal of Physiology-Cell Physiology* 2008, 294, C1509.
118. I. Khlistunova, M. Pickhardt, J. Biernat, Y. P. Wang, E. M. Mandelkow, E. Mandelkow, *Current Alzheimer Research* 2007, 4, 544.
119. P. Friedhoff, A. Schneider, E. M. Mandelkow, E. Mandelkow, *Biochemistry* 1998, 37, 10223.
120. M. Pickhardt, Z. Gazova, M. von Bergen, I. Khlistunova, Y. P. Wang, A. Hascher, E. M. Mandelkow, J. Biernat, E. Mandelkow, *Journal of Biological Chemistry* 2005, 280, 3628.
121. B. M. Trost, D. L. Vanvranken, *Journal of the American Chemical Society* 1990, 112, 1261
122. S. Takahashi, H. Terayama, H. Kuzuhara, *Tetrahedron Letters* 1991, 32, 5123.
123. M. Nakata, S. Akazawa, S. Kitamura, K. Tatsuta, *Tetrahedron Letters* 1991, 32, 5363.
124. N. S. Simpkins, S. Stokes, A. J. Whittle, *Tetrahedron Letters* 1992, 33, 793.
125. N. S. Simpkins, S. Stokes, A. J. Whittle, *Journal of the Chemical Society-Perkin Transactions* 1 1992, 2471.
126. B. M. Trost, D. L. Vanvranken, *Journal of the American Chemical Society* 1993, 115, 444.
127. T. Kitahara, N. Suzuki, K. Koseki, K. Mori, *Bioscience Biotechnology and Biochemistry* 1993, 57, 1906.
128. B. K. Goering, B. Ganem, *Tetrahedron Letters* 1994, 35, 6997.
129. D. A. Griffith, S. J. Danishefsky, *Journal of the American Chemical Society* 1996, 118, 9526.
130. T. J. Donohoe, C. P. Rosa, *Organic Letters* 2007, 9, 5509.
131. G. L. Huang, X. Y. Mel, H. C. Zhang, P. G. Wang, *Bioorganic & Medicinal Chemistry Letters* 2006, 16, 2860.
132. S. Takahashi, H. Terayama, H. Kuzuhara, *Tetrahedron Letters* 1994, 35, 4149.
133. M. Kinoshita, S. Sakuda, Y. Yamada, *Bioscience Biotechnology and Biochemistry* 1993, 57, 1699.

All citations are hereby incorporated by reference.

What is claimed is:
1. (3aR,4R,5R,6R,6aS)-6-(hydroxymethyl)-2-(methylamino)-4,5,6,6a-tetrahydro-3aH-cyclopenta[d]oxazole-4,5-diol, or a pharmaceutically acceptable salt thereof.
2. (3aR,4R,5R,6R,6aS)-2-(ethylamino)-6-(hydroxymethyl)-4,5,6,6a-tetrahydro-3aH-cyclopenta[d]oxazole-4,5-diol, or a pharmaceutically acceptable salt thereof.
3. (3aR,4R,5R,6R,6aS)-6-(hydroxymethyl)-2-(methylamino)-4,5,6,6a-tetrahydro-3aH-cyclopenta[d]thiazole-4,5-diol, or a pharmaceutically acceptable salt thereof.
4. (3aR,4R,5R,6R,6aS)-2-(ethylamino)-6-(hydroxymethyl)-4,5,6,6a-tetrahydro-3aH-cyclopenta[d]thiazole-4,5-diol or a pharmaceutically acceptable salt thereof.

* * * * *